United States Patent
Rescigno et al.

(10) Patent No.: US 10,695,363 B2
(45) Date of Patent: Jun. 30, 2020

(54) COMPOSITIONS AND METHODS FOR TREATING OR PREVENTING GUT PERMEABILITY-RELATED DISORDERS

(71) Applicant: Gelesis LLC, Boston, MA (US)

(72) Inventors: Maria Rescigno, Milan (IT);
Alessandro Sannino, Lecce (IT);
Yishai Zohar, Brookline, MA (US);
Elaine Chiquette, Boston, MA (US);
Alessandra Silvestri, Milan (IT);
Christian Demitri, San Pietro in Lama (IT)

(73) Assignee: Gelesis LLC, Boston, MA (US)

( * ) Notice: Subject to any disclaimer, the term of this patent is extended or adjusted under 35 U.S.C. 154(b) by 0 days.

(21) Appl. No.: 15/954,340

(22) Filed: Apr. 16, 2018

(65) Prior Publication Data

US 2018/0333428 A1    Nov. 22, 2018

Related U.S. Application Data

(60) Provisional application No. 62/562,665, filed on Sep. 25, 2017, provisional application No. 62/485,557, filed on Apr. 14, 2017.

(51) Int. Cl.
*A61K 31/717* (2006.01)
*A61K 9/00* (2006.01)
(Continued)

(52) U.S. Cl.
CPC .......... *A61K 31/717* (2013.01); *A61K 9/0053* (2013.01); *A61K 38/1825* (2013.01);
(Continued)

(58) Field of Classification Search
CPC .. A61K 47/38; A61K 38/1825; A61K 31/717; A61K 9/0053; Y02A 50/481; Y02A 50/473; Y02A 50/475
See application file for complete search history.

(56) References Cited

U.S. PATENT DOCUMENTS

| 5,380,522 A | 1/1995 | Day |
| 7,341,741 B1 | 3/2008 | Sachetto et al. |

(Continued)

FOREIGN PATENT DOCUMENTS

| EP | 0351987 B1 | 9/1992 |
| GB | 1538123 A | 1/1979 |

(Continued)

OTHER PUBLICATIONS

Dhandayuthapani, B., et al., "Polymeric Scaffolds in Tissue Engineering Application: A Review," International Journal of Polymer Science, 2011:1-19 (2011).

(Continued)

*Primary Examiner* — Jianfeng Song
(74) *Attorney, Agent, or Firm* — Elmore Patent Law Group, P.C.; Darlene A. Vanstone; Carolyn S. Elmore

(57) ABSTRACT

Compositions and methods are provided for treating a gut permeability-related disease or disorder comprising administering to the gastrointestinal tract of a subject in need thereof, a therapeutically effective amount of a hydrogel having an elastic modulus (G') of at least about 500 Pa.

15 Claims, 19 Drawing Sheets
(19 of 19 Drawing Sheet(s) Filed in Color)

(51) Int. Cl.
A61P 1/00 (2006.01)
A61K 47/38 (2006.01)
A61K 38/18 (2006.01)
A61L 31/14 (2006.01)
A61L 31/04 (2006.01)
A61L 31/16 (2006.01)

(52) U.S. Cl.
CPC .............. *A61K 47/38* (2013.01); *A61P 1/00* (2018.01); *A61L 31/042* (2013.01); *A61L 31/145* (2013.01); *A61L 31/16* (2013.01); *A61L 2300/232* (2013.01); *A61L 2300/412* (2013.01); *A61L 2300/60* (2013.01); *A61L 2430/34* (2013.01); *Y02A 50/473* (2018.01); *Y02A 50/475* (2018.01); *Y02A 50/481* (2018.01)

(56) References Cited

U.S. PATENT DOCUMENTS

| | | |
|---|---|---|
| 9,452,198 B2 | 9/2016 | Ribbeck et al. |
| 2002/0037919 A1 | 3/2002 | Hunter |
| 2006/0142794 A1 | 6/2006 | Lendlein et al. |
| 2009/0311235 A1 | 12/2009 | Elenko et al. |
| 2012/0301546 A1 | 11/2012 | Hassan |
| 2013/0089737 A1* | 4/2013 | Sannino ............... C08B 3/12 428/402 |
| 2013/0259870 A1 | 10/2013 | Traber et al. |
| 2016/0022862 A1 | 1/2016 | Alsberg |
| 2016/0222134 A1* | 8/2016 | Sannino ............... C08B 15/005 |

FOREIGN PATENT DOCUMENTS

| | | |
|---|---|---|
| WO | 98/01112 A1 | 1/1998 |
| WO | 2015/120471 A1 | 8/2015 |
| WO | 2015/162447 A1 | 10/2015 |

OTHER PUBLICATIONS

Hsieh, C-Y, et al., "Strengthening of the intestinal epithelial tight junction by Bifidobacterium bifidum," Physiol Rep, 3(3): 1-17 (2015).
Piraino, F., et al., "A Current View of Functional Biomaterials for Wound Care, Molecular and Cellular Therapies," BioMed Research International, 15: 1-10 (2015).
"H. Pylori & Peptic Ulcer," Wake Gastro., pp. 1-6 (2016).
Crouzier, T., et al., "Modulating Mucin Hydration and Lubrication by Deglycosylation and Polyethylene Glycol Binding," Adv. Mater. Interfaces, 2: 1-7 (2015).
Odenwald, M. A., et al., "The intestinal epithelial barrier: a therapeutic target?" Nature Reviews, 14: 9-21 (2017).
Spadoni, I., et al., "A gut-vascular barrier controls the systemic dissemination of bacteria," Sciencemag.org, Science, 350(6262): 830-834 (2015).
Eisenstein, M., "Biology: A slow-motion epidemic," Nature, 540 (2016).
Bischoff, S. C., et al., "Intestinal permeability—a new target for disease prevention and therapy," BMC Gastroenterology, 14 (2014).
Brandl, K., et al., "Gut-liver axis at the frontier of host-microbial interactions," Articles in PresS. Am J Physiol Gastrointest Liver Physiol, (2017).
Brandl, K., et al., Is intestinal inflammation linking dysbiosis to gut barrier dysfunction during liver disease? Expert Rev Gastroenterol Hepatol., 9(8): 1069-1076 (2015).
Nobel, E. E., et al., "Gut to Brain Dysbiosis: Mechanisms Linking Western Diet Consumption, the Microbiome,and Cognitive Impairment," Frontiers in Behavioral Neuroscience, 11(9): 1-10 (2017).
Galactomannan, from Wikipedia. Retrieved from the internet on Oct. 29, 2018. <<https://en.wikipedia.org/wiki/Galactomannan>>.
"Researchers discover mechanism for fixing defective mucins," Oct. 2, 2015 <<https://phys.org/news/2015-10-mechanism-defective-mucins.html>>.
Wong, C., et al., "Potential Benefits of Dietary Fibre Intervention in Inflammatory Bowel Disease," Int. J. Mol. Sci., 17(919): 1-22 (2016).
Miele, L. et al., "Increased intestinal permeability and tight junction alterations in nonalcoholic fatty liver disease," Hepatology, 49(6): 1877-1887 (2009).
Strugala, V., et al., "Thickness and continuity of the adherent colonic mucus barrier in active and quiescent ulcerative colitis and Crohn's disease," Int. J. Clin. Pract., 62(5): 762-769 (2008).
Van Der Sluis, M., et al., "Muc2-Deficient Mice Spontaneously Develop Colitis, Indicating That MUC2 is Critical for Colonic Protection," Gastroenterology, 131(1): 117-129 (2006).
Lamprecht, A., et al., "Size-Dependent Bioadhesion of Micro- and Nanoparticulate Carriers to the Inflamed Colonic Mucosa," Pharm. Res., 18(6): 788-793 (2001).
Hamman, J. H., "Composition and Applications of Aloe vera Leaf Gel," Molecules, 13: 1599-1616 (2008).
Hay, W. P., et al., "One Percent Sodium Carboxymethylcellulose Prevents Experimentally Induced Abdominal Adhesions in Horses," Veterinary Surgery, 30(3): 223-227 (2001).
Zhu, J., et al., "Design properties of hydrogel tissue-engineering scaffolds," Expert Rev. Med. Devices, 8(5): 607-626 (2011).
Nikode, S., et al., "In Situ Gel: Application and Uses of Polymers", World J. Pharmacy and Pharmaceutical Sciences, 5(7): 1638-1658 (2016).
Ahmed, J., A., et al., "A Conceptual Overview on Superporous Hydrogels," Int. J. Pharm. Sci. Rev. Res., 25(2): 166-173 (2014).
Ray, D., et al., "Designing of Superporous cross-linked hydrogels containing acrylic based polymer network," Asian J. Pharmaceutics: 123-127 (2008).
Volod'Ko, A. V., et al., "Soluble Chitosan-Carrageenan Polyelectrolyte Complexes and Their Gastroprotective Activity," Carbohydrate Polymers, 101: 1087-1093 (2014).
Michielan, A., et al., "Intestinal Permeability in Inflammatory Bowel Disease: Pathogenesis, Clinical Evaluation, and Therapy of Leaky Gut," Mediators of Inflammation, vol. 2015, Article ID 628157. Hindawi Publishing Corporation.
Spengler, E., et al., "The Gut Microbiota, Intestinal Permeability, Bacterial Translocation, and Nonalcoholic Fatty Liver Disease: What Comes First?" Cellular and Molecular Gastroenterology and Hepatology, 1:129-130 (2015).
Keefe, D. M. K., et al., "Effect of high-dose chemotherapy on intestinal permeability in humans," Clinical Science, 92: 385-389 (1997).
Silvestri, A., et al., "GELESIS Novel, Non-Systemic, Superabsorbent Hydrogel Improves Intestinal Barrier Function in Intestinal Injury Pre-Clinical Model," poster presented at the Endocrine Society annual meeting (ENDO 2019, New Orleans, LA).
Silvestri, A. et al., "GELESIS Superabsorbent Hydrogel Prevents Hepatic Steatosis and Insulin Resistance in High Fat Diet-Induced NAFLD Pre-Clinical Model," poster presented at Europeans Association for the Study of the Liver (EASL) International Liver Congress 2019, Vienna Austria, Apr. 10, 2019.
Gäbele, E., et al., "DSS induced colitis increases portal LPS levels and enhances hepatic inflammation and fibrogenesis in experimental NASH," Journal of Hepatology, vol. 55: 1391-1399 (2011).
Henao-Mejia. J., et al., "Inflammasome-mediated dysbiosis regulates progression of NAFLD and obesity," Nature, 482(7384): 179-185 (2012).

* cited by examiner

COMPOSITIONS AND METHODS FOR TREATING OR PREVENTING GUT PERMEABILITY-RELATED DISORDERS

BACKGROUND OF THE INVENTION

The gastrointestinal (GI) tract in humans refers to the stomach and the intestine and sometimes to all the structures from the mouth to the anus. The upper gastrointestinal tract consists of the esophagus, stomach and duodenum. Some sources also include the mouth cavity and pharynx. The exact demarcation between "upper" and "lower" can vary. Upon gross dissection, the duodenum may appear to be a unified organ, but it is often divided into two parts based upon function, arterial supply, or embryology. The integrated part of GI tract is pancreas and liver named the accessory organs of GI tract.

The lower gastrointestinal tract includes most of the small intestine and all of the large intestine. According to some sources, it also includes the anus. The intestine—or bowel—is divided into the small intestine and the large intestine. The small intestine has three parts: i) duodenum where the digestive juices from pancreas and liver mix together, ii) jejenum which is the midsection of the intestine, connecting duodenum to ileum and iii) ileum which has villi in where all soluble molecules are absorbed into the blood. The large intestine also has three parts: i) caecum where the vermiform appendix is attached to the cecum, ii) colon which consists of the ascending colon, transverse colon, descending colon and sigmoid flexure, and iii) rectum.

The intestine has two main roles: digestion and absorption of nutrients, and maintenance of a barrier against the external environment. It also forms the largest endocrine organ in the body as well as the largest and most complex part of the immune system. In human adults, the intestinal surface area is large, about 100 $m^2$. This large area is continuously exposed to different antigens in the form of food constituents, normal intestinal microflora and pathogens.

The intestinal mucosal surface, also referred to herein as "intestinal tissue", is lined by a single layer of epithelial cells (IEC) which are continuously and rapidly replaced by replication of undifferentiated cells within the crypt ($7\times10^6$ cell/min). The epithelial cell layer of the intestinal mucosa is very complex and unique. It secretes digestive enzymes from the apical part to lumen for food digestion. It also secretes different proteins from the second half to the lamina propria (LP). Further, said epithelial cells are receiving signals from both the lumen (and then transmitting the information to the diverse populations of cells in the LP) and the basolateral side. On the basolateral side the intestinal epithelial cells (IECs) receive many signals from various immune cells, nerve cells and stromal cells. Signals on both sides are affected by their respective microenvironments, influencing the functional states, behaviors, and structures of enterocytes resulting in integrity and homeostasis of the gastrointestinal tract.

The protection of the epithelial barrier is guaranteed by junctional complexes composed by tight junctions (TJ) and adherens junctions (AJ) that seal epithelial cells and by production of mucus. The mucus produced also by the specialized epithelial cells, namely goblet cells, provides the first line of defense physical and chemical injury caused by ingested food, microbes and bacterial products. Damage to any part of the GI tract including the goblet cells may lead to an impaired gut barrier, allowing entry of luminal contents into the intestinal wall and initiating chronic inflammation, including inflammation of the GI tract. There is a need for new compositions and methods for preventing and treating gut permeability-related diseases and disorders.

SUMMARY OF THE INVENTION

Compositions and methods are provided for preventing and treating gut permeability-related diseases and disorders, including gastrointestinal inflammation, comprising administering to the gastrointestinal tract of a subject in need thereof, a therapeutically and homeostatic effective amount of a hydrogel, preferably a hydrogel having an elastic modulus (G'), as defined herein, of at least about 500 Pa, preferably from about 500 Pa to about 8,000 Pa, and more preferably from about 500 Pa to about 10,000 Pa.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
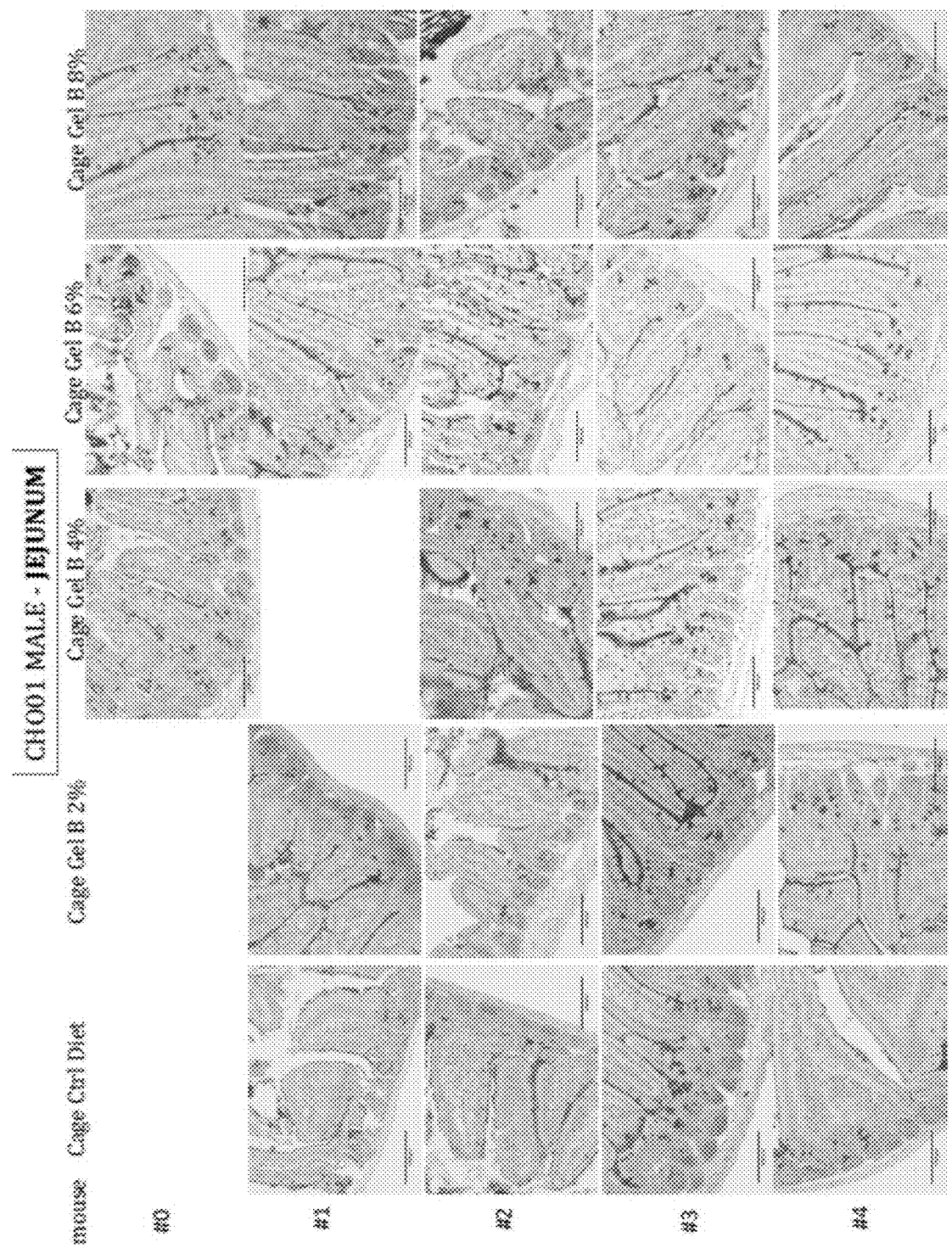
FIG. 1 is an image of the stained jejunum of control mice and mice treated with a hydrogel of the invention stained with Alcian Blue-PAS for mucus visualization.

As used herein, the singular forms "a", "and", and "the" include plural referents unless the context clearly dictates otherwise. Thus, for example, reference to "a biomarker" includes a plurality of such biomarkers.

For the purposes of the invention, the "gastrointestinal tract", or "GI tract" is understood to include the stomach, small intestine (duodenum, jejunum, ileum), large intestine (cecum, colon, rectum) and anus. The lower gastrointestinal tract includes most of the small intestine and all of the large intestine. According to some sources, it also includes the anus. The "intestine" is divided into the small intestine and the large intestine. The small intestine has three parts: i) duodenum where the digestive juices from pancreas and liver mix together, ii) jejunum which is the midsection of the intestine, connecting duodenum to ileum and iii) ileum which has villi in where all soluble molecules are absorbed into the blood. The large intestine also has three parts: i) cecum where the vermiform appendix is attached to the cecum, ii) colon which consists of the ascending colon, transverse colon, descending colon and sigmoid flexure, and iii) rectum. As used herein tissues lining gastrointestinal tract may be referred to as "intestinal tissue", "mucosal surface", "mucosal tissue" or "mucosa".

The term "gut permeability-related disease or disorder" refers to a disease or disorder which is associated with disturbed intestinal permeability which is increased compared to normal permeability and leads to loss of intestinal homeostasis, functional impairment and disease. A subject can be identified as suffering from disturbed intestinal permeability by measuring the intestinal permeability of the subject, using known intestinal permeability assays and/or assessment of markers of epithelial integrity, including adhesion molecules, biomarkers of immunity or inflammation or bacterial markers, such as endotoxin (Bischoff et al., BC Gastroenterology 2014, 14:189). A subject can also be identified as suffering from disturbed intestinal permeability upon diagnosis of the subject with a gut permeability-related disease or disorder, such as described herein.

A "therapeutically effective amount", or "effective amount", or "therapeutically effective", as used herein, refers to that amount which provides a therapeutic effect for a given condition and administration regimen; for example, an amount sufficient to maintain healthy gut epithelial tissue, prevent damage to healthy gut epithelial tissue resulting from, for example, gut permeability-related diseases or adverse side effects of medications, repair and regenerate intestinal tissue and/or reduce the pathology, signs or symptoms of a gut permeability-related disease or disorder, such as inflammation in the GI tract. This is a predetermined quantity of active material calculated to produce a desired therapeutic effect in association with the required additive and diluent, i.e. a carrier or administration vehicle. Further, it is intended to mean an amount sufficient to reduce or prevent a clinically significant deficit in the activity, function and response of patient. Alternatively, a therapeutically effective amount is sufficient to cause an improvement in a clinically significant condition in a patient. As is appreciated by those skilled in the art, the amount of a compound may vary depending on its specific activity. Suitable dosage amounts may contain a predetermined quantity of active composition calculated to produce the desired therapeutic effect in association with the required diluent.

A "subject" or "patient" refers to a human, primate, non-human primate, laboratory animal, farm animal, livestock, or a domestic pet.

The term "treat" or "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein a "hydrogel" is a hydrophilic polymer or combination of two or more hydrophilic polymers that are capable of retaining a large relative volume of aqueous solution. Hydrogels may be branched or linear or a mixture of branched and linear polymers, e.g., about 1, 2, 3, 4, 5, 10, 15, 20, 30, 40, 50, 60, 70, 80, 90, 95, 96, 97, 98, 99, or 100% (w/w) linear versus branched. In preferred embodiments, the hydrophilic polymer or polymers are crosslinked, for example, via physical, ionic or covalent crosslinks. Hydrogels can have various amounts of cross-linking, depending on the desired physical properties of the hydrogel. Preferably hydrogels used in the methods of the invention have elastic properties that are optimized for treatment or prevention of gut permeability-related diseases and disorders in accordance with the invention. The elastic properties of the hydrogels of use in the methods of the invention are related to their macromolecular structure, including the degree of cross linking, type of cross linking agent, molecular weight and structure of the backbone. Preferably, the hydrogel does not include a plasticizer. Suitable hydrogels useful in the methods of the invention include those disclosed in U.S. Pat. Nos. 9,353,191 and 8,658,147 and U.S. Patent Pub.: 2016/0222134 and U.S. application Ser. No. 15/944,960, the contents of each of which are incorporated by reference herein in their entirety.

As used herein, the term "hydrophilic polymer" refers to a polymer which is substantially water-soluble and, preferably, includes monomeric units which are hydroxylated. A hydrophilic polymer can be a homopolymer, which includes only one repeating monomeric unit, or a copolymer, comprising two or more different repeating monomeric units. In certain embodiments, the hydrophilic polymer is an addition polymer or a condensation polymer. A portion or all of the repeating units of a hydrophilic polymer comprise a polar functional group, for example, an acidic, basic or neutral hydrophilic functional group, for example, hydroxyl; carboxyl; sulfonate, phosphonate; guanidine; amandine; primary, secondary, or tertiary amino; or quaternary ammonium. In a preferred embodiment, the hydrophilic polymer is hydroxylated, such as polyallyl alcohol, polyvinyl alcohol or a polysaccharide. Examples of suitable polysaccharides include modified celluloses, including substituted celluloses, substituted dextrans, starches and substituted starches, glycosaminoglycans, chitosan and alginates.

In certain embodiments, the hydrogel comprises a crosslinked addition polymer, such as a crosslinked polyacrylate, a crosslinked polymethacrylate or a crosslinked copolymer of either arcrylate or methacrylate with a neutral monomer, such as acrylamide or methacrylamide. Such polymers and copolymers can be crosslinked using methods known in the art. In certain embodiments, the hydrogel comprises polyethylene glycol diacrylate (PEGDA). Preferably the average molecular weight of PEGDA ranges from about 250 Da to about 20,000 Da. Preferably the average molecular weight of PEGDA is 250 DA, 575 Da, 700 Da, 750 Da, 1000, Da, 2000 Da, 6,000 Da, 10,000 Da or 20,000 Da.

Polysaccharides which can be used in the hydrogels of the invention include modified celluloses, such as cellulose esters and ethers. Cellulose esters include cellulose acetate, cellulose acetate propionate and cellulose acetate butyrate. Cellulose ethers include alkylcelluloses, such as $C_1$-$C_6$-alkylcelluloses, including methylcellulose, ethylcellulose and n-propylcellulose; substituted alkylcelluloses, including hydroxy-$C_1$-$C_6$-alkylcelluloses and hydroxy-$C_1$-$C_6$-alkyl-$C_1$-$C_6$-alkylcelluloses, such as hydroxyethylcellulose, hydroxy-n-propylcellulose, hydroxy-n-butylcellulose, hydroxypropylmethylcellulose, ethylhydroxyethylcellulose and carboxymethylcellulose; starches and substituted starches, such as corn starch, hydroxypropylstarch and carboxymethylstarch; substituted dextrans, such as dextran sulfate, dextran phosphate and diethylaminodextran; glycosaminoglycans, including heparin, hyaluronan, chondroitin, chondroitin sulfate and heparan sulfate; and polyuronic acids, such as polyglucuronic acid, polymanuronic acid, polygalacturonic acid and polyarabinic acid.

As used herein, the term "ionic polymer" refers to a polymer comprising monomeric units having an acidic functional group, such as a carboxyl, sulfate, sulfonate, phosphate or phosphonate group, or a basic functional group, such as an amino, substituted amino or guanidyl group. When in aqueous solution at a suitable pH range, an ionic polymer comprising acidic functional groups will be a polyanion, and such a polymer is referred to herein as an "anionic polymer". Likewise, in aqueous solution at a suitable pH range, an ionic polymer comprising basic functional groups will be a polycation. Such a polymer is referred to herein as a "cationic polymer". As used herein, the terms ionic polymer, anionic polymer and cationic polymer refer to hydrophilic polymers in which the acidic or basic functional groups are not charged, as well as polymers in which some or all of the acidic or basic functional groups are charged, in combination with a suitable counterion. Suitable anionic polymers include alginate, dextran sulfate, carboxymethylcellulose, hyaluronic acid, polyglucuronic acid, polymanuronic acid, polygalacturonic acid, polyarabinic acid; chrondroitin sulfate and dextran phosphate. Suitable cationic polymers include chitosan and dimethylaminodextran. A preferred ionic polymer is carboxymethylcellulose, which can be used in the acid form, or as a salt with a suitable cation, such as sodium or potassium.

The term "nonionic polymer", as used herein, refers to a hydrophilic polymer which does not comprise monomeric units having ionizable functional groups, such as acidic or basic groups. Such a polymer will be uncharged in aqueous solution. Examples of suitable nonionic polymers for use in the present method are polyallylalcohol, polyvinylalcohol, starches and substituted starches, such as corn starch and hydroxypropylstarch, mannans, glucomannan, acemannans, alkylcelluloses, such as $C_1$-$C_6$-alkylcelluloses, including methylcellulose, ethylcellulose and n-propylcellulose; substituted alkylcelluloses, including hydroxy-$C_1$-$C_6$-alkylcelluloses and hydroxy-$C_1$-$C_6$-alkyl-$C_1$-$C_6$-alkylcelluloses, such as hydroxyethylcellulose (HEC), hydroxy-n-propylcellulose, hydroxy-n-butylcellulose, hydroxypropylmethylcellulose, and ethylhydroxyethylcellulose.

Preferably the hydrogels used in the methods of the invention are cross-linked. Cross-linking can be achieved either through covalent cross-linking or non-covalent cross-linking. Covalent crosslinking can be achieved using a bifunctional cross-linking agent (also referred to herein as a bifuctional "cross-linker"), or by direct reaction of functional groups on two different polymer strands. Typical covalent cross-linkers of the present invention include, for example, homobifunctional cross-linkers with reactive functional groups, such as diglycidyl ethers, substituted and unsubstituted di-N-hydroxy succinimides (NETS), diisocyanates, diacids, diesters, diacid chlorides, dimaleimides, diacrylates, and the like. Heterobifunctional cross-linkers can also be utilized. Heterobifunctional cross-linkers usually include molecules that contain different reactive functional groups to accomplish the cross-linking, for example, combining NHS and maleimide, an acid and ester, etc. Covalent crosslinking can also be achieved by irradiation of a hydrophilic polymer or a combination of hydrophilic polymers, for example with x-rays or an electron beam.

Non-covalent cross-linking, e.g., based on ionic bonds, hydrogen bonding, hydrophobic interactions and other intramolecular associations are also contemplated for use in the practice of the invention.

Preferred hydrogels of the invention are crosslinked using a crosslinking agent such as a polycarboxylic acid. As used herein, the term "polycarboxylic acid" refers to an organic acid having two or more carboxylic acid functional groups, such as dicarboxylic acids, tricarboxylic acids and tetracarboxylic acids, and also includes the anhydride forms of such organic acids. Dicarboxylic acids include oxalic acid, malonic acid, maleic acid, malic acid, succinic acid, glutaric acid, adipic acid, pimelic acid, suberic acid, azelaic acid, sebacic acid, phthalic acid, o-phthalic acid, isophthalic acid, m-phthalic acid, and terephthalic acid. Preferred dicarboxylic acids include $C_4$-$C_{12}$-dicarboxylic acids. Suitable tricarboxylic acids include citric acid, isocitric acid, aconitic acid, and propane-1,2,3-tricarboxylic acid. Suitable tetracarboxylic acids include pyromellitic acid, 2,3,3',4'-biphenyltetracarboxylic acid, 3,3',4,4'-tetracarboxydiphenylether, 2,3',3,4'-tetracarboxydiphenylether, 3,3',4,4'-benzophenonetetracarboxylic acid, 2,3,6,7-tetracarboxynaphthalene, 1,4,5,7-tetracarboxynaphthalene, 1,4,5,6-tetracarboxynaphthalene, 3,3',4,4'-tetracarboxydiphenylmethane, 2,2-bis(3,4-dicarboxyphenyl)propane, butanetetracarboxylic acid, and cyclopentanetetracarboxylic acid. A particularly preferred polycarboxylic acid is citric acid.

Preferably, a hydrogel of the invention is covalently cross-linked. Preferably the hydrogel has an elastic modulus (G') when swollen in SGF/water (1:8) of at least 500 Pa, as determined according to the method described in Example 2. Preferably, a hydrogel of the invention has a G' when swollen in SGF/water (1:8) of at least about 500 Pa, preferably at least about 700, preferably at least about 800, preferably at least about 1000 Pa, preferably at least about 1500 Pa, preferably at least about 2000 Pa, preferably at least about 3000 Pa at least about 3500 Pa, preferably at least about 4000 Pa preferably at least about 4500 Pa, preferably at least about 5000 Pa preferably at least about 5500 Pa, preferably at least about 6000 Pa, preferably at least about 6500 Pa, preferably at least about 7000 Pa, preferably at least about 7500 Pa, preferably at least about 8000 Pa, preferably at least about 8500 Pa. Preferably, the hydrogel is crosslinked carboxymethylcellulose having a G' when swollen in SGF/water (1:8) from about 500 Pa to about 1500 Pa, from about 500 Pa to about 800 Pa, from about 500 Pa to about 1000 Pa, from about 1500 Pa to about 8000 Pa, from about 5000 Pa to about 8000 Pa, from about 5000 Pa to about 5500 Pa, from about 6000 Pa to about 8000 Pa or from about 6500 Pa to about 8000 Pa.

Preferably, a covalently cross-linked hydrogel of the invention has an elastic modulus (G') when swollen in SGF/water (1:8) of at least about 500 Pa to about 10,000 Pa, preferably at least about 600 Pa to about 9,000 Pa, preferably at least about 800 Pa to about 8,000 Pa, and preferably at least about 1,000 Pa to about 6,000 Pa.

Preferably, a covalently cross linked hydrogel of the invention has a G' when swollen in SGF/water (1:8) from about 500 Pa to about 9,000 Pa, from about 500 Pa to about 6,000 Pa, from about 500 Pa to about 5,000 Pa, from about 1,000 Pa to about 10,000 Pa, from about 1,000 Pa to about 8,000 Pa, from about 1,000 Pa to about 5500 Pa, from about 1,200 Pa to about 10,000 Pa or from about 1,200 Pa to about 8000 Pa. Preferred hydrogels have similar elastic and/or absorbency properties when swollen in SGF/water (1:8) and simulated intestinal fluid (SIF). For example, preferred hydrogels have a G' when swollen in SIF which is within 20% of the G' when swollen in SGF/water (1:8). Preferred hydrogels have an MUR in SIF which is within 20% of the MUR in SGF/water (1:8).

Preferred hydrogels of the invention (covalently cross-linked, non-covalently crosslinked, or uncrosslinked), have similar elastic and/or absorbency properties when swollen in SGF/water (1:8) and simulated intestinal fluid (SIF). For example, preferred hydrogels have a G' when swollen in SIF which is within 20% of the G' when swollen in SGF/water (1:8). Preferred hydrogels have an MUR in SIF which is within 20% of the MUR in SGF/water (1:8).

Preferably the hydrogel of the invention comprises any hydrogel polymer capable of maintaining the preferred elastic modulus (G') properties during transit throughout the GI tract. Preferably the hydrogel remains stable during transit throughout the GI tract including the colon. Alternatively, a preferred hydrogel may degrade or partially degrade during the transit through the colon. Alternatively, a preferred hydrogel may partially degrade during transit through the small intestine and or the colon. Partial degradation of the hydrogel may be achieved by stabilizing copolymers in the network, where one or more of the polymers are degradable in different parts of the GI tract. An example of such a mechanism, without limitation, is the crosslinking of CMC and chitosan, or CMC and glucomannan, for example, with citric acid or a bifunctional polyethylene glycol (PEG). These copolymer backbones are able to provide such a partial degradation approach. The CMC portion will degrade in the colon while the chitosan or glucomannan portion will remain stable, maintaining a high elastic modulus. Alternatively, partial degradation can be achieved by homopolymers, using different cross-linkers, when one or more of the cross linkers are degradable in different GI tracts. An example is a cellulose derivative crosslinked with citric acid and bifunctional PEG, where the citric acid crosslinks will degrade while the PEG crosslinks will not. Partial degradation may be achieved by a combination of the techniques described above. Once the hydrogel is partially degraded, either by polymer and/or cross linker degradation, the elastic response to deformation, which is entropic in nature, decreases. Thus, the elastic modulus decreases accordingly. Partial degradation can be used as a tool to adjust the elastic modulus of the hydrogels described in these methods during their transit in different GI tracts. In addition to the ionic polymers discussed below suitable polymers of the invention include the following polymers in crosslinked or uncrosslinked form and include uncrosslinked polymers capable of self-crosslinking once deployed in the GI tract form including but are not limited to: HEC, chitosan, glucomannan, starch, acrylates microcrystalline cellulose, psyllium, and guar gum.

One preferred crosslinker is poly(ethylene glycol) diglycidyl ether (PEGDE). The term "bifunctional polyethylene glycol" and "bifunctional PEG" are used interchangeably herein and refer to a polyethylene glycol polymer which is functionalized at each end with a terminal reactive functional group. Suitable reactive groups include those which are able to react with complementary groups in the polysaccharide, such as hydroxyl, carboxyl and amino groups, to form a covalent bond. Suitable such groups include azide, thiol, succinimide, epoxide, carboxy, amino, ethenyl, ethynyl, nitrophenyl, and bromoalkyl groups. Preferably, the functional group is stable in water at neutral pH. A preferred functional group is epoxide. The PEG unit of the bifunctional PEG can be of any suitable length and is generally characterized by the number average molecular weight ($M_n$) of the bifunctional PEG. In certain embodiments, the bifunctional PEG has an $M_n$ from about 150 Da to about 1,000,000 DA, preferably from 200 Da to 100,000 Da, preferably from 250 Da to 50,000 Da, preferably from 200 Da to 10,000 Da, more preferably from 250 Da to 5000 Da, 400 Da to 2500 Da, 250 Da to 1000 Da, 350 Da to 650 Da, 450 Da to 550 Da or about 500 Da to about 550 Da. Preferably the bifunctional PEG is poly(ethylene glycol) diglycidyl ether (PEGDE) having a molecular weight from about 450 Da to about 600 Da, or about 500 Da to about 550 Da or about 520 Da to about 530 Da. Preferably PEGDE has an average molecular weight from about or about 400 Da to about 10,000 Da, preferably about, 400 Da to about 8,000 Da, preferably about 400 Da to 6,000 Da, preferably about 460 Da to about 4,600 Da, preferably about 460 Da to about 3,000 Da. Preferably, the bifunctional PEG is PEGDE and the weight ratio of the polymer(s), for example, polysaccharide(s) to PEGDE in the solution of step (1) is from about 20 w/w to about 20000 w/w, preferably about 50 w/w to about 10000 w/w and more preferably about 100 w/w to about 1000 w/w.

Preferably, the hydrogel of the invention comprises an ionic polymer, preferably an anionic polymer, and most preferably, carboxymethylcellulose. Preferably, the anionic polymer is carboxymethylcellulose which is covalently crosslinked with citric acid or a bifunctional PEG as described herein.

In certain embodiments, the hydrogel of the invention comprises an ionic polymer and a non-ionic polymer. The ionic polymer is preferably an anionic polymer, and most preferably, carboxymethylcellulose. The non-ionic polymer is preferably a non-ionic polysaccharide, such as a substituted cellulose, glucomannan, guar gum or psyllium. In other embodiments, the non-ionic polymer is a hydroxyalkylcellulose, such as hydroxyethylcellulose ("HEC") or a hydroxyalkyl alkylcellulose. In certain embodiments, the ionic polymer is crosslinked with the non-ionic polymer, for example, with a crosslinking agent such as a polycarboxylic acid, preferably citric acid, or a bifunctional PEG, such as PEGDE. The weight ratios of the ionic and non-ionic polymers (ionic:non-ionic) can range from about 1:10 to about 10:1, preferably from about 1:5 to about 5:1. In preferred embodiments, the weight ratio is greater than 1:1, for example, from about 2 to about 5. In a particularly preferred embodiment, the ionic polymer is carboxymethycellulose, the non-ionic polymer is hydroxyethylcellulose, and the weight ratio (ionic:nonionic) is about 3:1.

Most preferably, the invention provides a crosslinked carboxymethylcellulose, for example a citric acid crosslinked carboxymethylcellulose, which has an elastic modulus (G') when swollen in SGF/water (1:8) of at least 1500 Pa, as determined according to the method described in Example 2. Preferably, the crosslinked carboxymethylcellulose has a G' when swollen in SGF/water (1:8) of at least about 500 Pa, preferably at least about 700, preferably at least about 800, preferably at least about 1500 Pa, preferably at least about 2000 Pa, preferably at least about 3000 Pa at least about 3500 Pa, preferably at least about 4000 Pa preferably at least about 4500 Pa, preferably at least about 5000 Pa preferably at least about 5500 Pa, preferably at least about 6000 Pa, preferably at least about 6500 Pa, preferably at least about 7000 Pa, preferably at least about 7500 Pa, preferably at least about 8000 Pa, preferably at least about 8500 Pa. Preferably, the citric acid crosslinked carboxymethylcellulose of the invention has a G' when swollen in SGF/water (1:8) from about 1500 Pa to about 8000 Pa, from about 5000 Pa to about 8000 Pa, from about 5000 Pa to about 5500 Pa, from about 6000 Pa to about 8000 Pa or from about 6500 Pa to about 8000 Pa.

Most preferably, the invention provides a crosslinked carboxymethylcellulose, for example a citric acid crosslinked carboxymethylcellulose having an elastic modulus (G') when swollen in SGF/water (1:8) of at least about 500 Pa to about 10,000 Pa, preferably at least about 600 Pa to about 9,000 Pa, preferably at least about 800 Pa to about 8,000 Pa, and preferably at least about 1,000 Pa to about 6,000 Pa.

Most preferably, the invention provides a crosslinked carboxymethylcellulose, for example a citric acid crosslinked carboxymethylcellulose having a G' when swollen in SGF/water (1:8) from about 500 Pa to about 9,000 Pa, from about 500 Pa to about 6,000 Pa, from about 500 Pa to about 5,000 Pa, from about 1,000 Pa to about 10,000 Pa, from about 1,000 Pa to about 8,000 Pa, from about 1,000 Pa to about 5500 Pa, from about 1,200 Pa to about 10,000 Pa or from about 1,200 Pa to about 8000 Pa. Preferred hydrogels have similar elastic and/or absorbency properties when swollen in SGF/water (1:8) and simulated intestinal fluid (SIF). For example, preferred hydrogels have a G' when swollen in SIF which is within 20% of the G' when swollen in SGF/water (1:8). Preferred hydrogels have an MUR in SIF which is within 20% of the MUR in SGF/water (1:8).

Preferably, the crosslinked carboxymethylcellulose has a G' when swollen in SGF/water (1:8) of at least about from about 500 Pa to about 1500 Pa, from about 500 Pa to about 800 Pa, from about 500 Pa to about 1000 Pa, from about 1500 Pa to about 8000 Pa, from about 5000 Pa to about 8000 Pa, from about 5000 Pa to about 5500 Pa, from about 6000 Pa to about 8000 Pa, from about 6500 Pa to about 8000 Pa from about. 5000 Pa to about 5500 Pa; or a G' of at least about 2700 Pa.

Carboxymethylcellulose is commercially available in a wide range of molecular weights. It is generally most convenient to express the molecular weight of a sodium carboxymethylcellulose in terms of the viscosity of a 1.0% (wt/wt) sodium carboxymethylcellulose solution in water at 25 C. Carboxymethylcelluloses suitable for use in the present invention preferably form a 1% (wt/wt) solution in water having a viscosity under these conditions from about 50 centipoise (cps) to about 11,000 cps, more preferably from about 500 cps to about 11000 cps. In certain embodiments, the viscosity of the solution under these conditions is from about 1000 cps to about 11000 cps, about 1000 cps to about 2800 cps, about 1500 cps to about 3000 cps, about 2500 to about 6000 cps. In certain embodiments, the viscosity of the solution under these conditions is from about 6000 cps to about 11000 cps. The viscosity of the carboxymethylcellulose solution is determined according to the method set forth in Example 2 which is in accordance with ASTM D1439-03(2008)e1 (ASTM International, West Conshohocken, Pa. (2008), incorporated herein by reference in its entirety).

In one embodiment, the hydrogel is produced by crosslinking high viscosity carboxymethylcellulose. The high viscosity carboxymethylcellulose can be covalently crosslinked or physically crosslinked. For example, the high viscosity carboxymethylcellulose can be covalently crosslinked, for example, with a suitable, preferably physiologically acceptable bifunctional crosslinking agent. In one embodiment, the high viscosity carboxymethylcellulose is crosslinked with a polycarboxylic acid, such as citric acid. In another embodiment, the high viscosity carboxymethylcellulose is crosslinked with a bifunctional PEG, such as PEGDE., Polymer hydrogels formed by crosslinking high viscosity carboxymethylcellulose with citric acid are described in US 2016/0222134, the contents of which are incorporated herein by reference in their entirety.

The term "high viscosity carboxymethylcellulose", as used herein, refers to carboxymethylcellulose, as the sodium salt, which forms a 1% (wt/wt) solution in water having a viscosity of at least 1500 cps. In preferred embodiments, the high viscosity carboxymethylcellulose also has a low polydispersity index, such as a polydispersity index of about 8 or less. Preferably, the high viscosity carboxymethylcellulose preferably forms a 1% (wt/wt) solution in water having a viscosity at 25° C. of at least about 1500, 2,000, 3000, 4000, 5000, 6000, 7000, 7500, or 8000 cps. In certain embodiments, the carboxymethylcellulose forms a 1% (wt/wt) aqueous solution having a viscosity of 6000 to about 10000 cps or about 6000 to 11000 cps at 25° C. In certain embodiment, the carboxymethylcellulose forms a 1% (wt/wt) aqueous solution having a viscosity of about 6000 to about 9500 cps or about 7000 to 9500 cps at 25° C. In another embodiment, the carboxymethylcellulose forms a 1% (wt/wt) aqueous solution having a viscosity of about 7000 to about 9200 cps or about 7500 to 9000 cps at 25° C. In yet another embodiment, the carboxymethylcellulose forms a 1% (wt/wt) aqueous solution having a viscosity of about 8000 to about 9300 cps, or about 9000 cps at 25° C. Preferably the carboxymethylcellulose is in the form of the sodium salt. Preferably, the carboxymethylcellulose is sodium carboxymethylcellulose which forms a 1% (wt/wt) aqueous solution having a viscosity of about 7800 cps or higher, for example, from about 7800 to 11000 cps, or about 8000 cps to about 11000 cps.

In preferred embodiments, the high viscosity carboxymethylcellulose further has a polydispersity index (Mw/Mn) of about 8 or less, preferably about 7 or less, or 6 or less. In one embodiment, the polydispersity index is from about 3 to about 8, about 3 to about 7, about 3 to about 6.5, about 3.0 to about 6; about 3.5 to about 8, about 3.5 to about 7, about 3.5 to about 6.5, about 3.5 to about 6, about 4 to about 8, about 4 to about 7, about 4 to about 6.5, about 4 to about 6, about 4.5 to about 8, about 4.5 to about 7, about 4.5 to about 6.5, about 4.5 to about 6, about 5 to about 8, about 5 to about 7.5, about 5 to about 7, about 5 to about 6.5, or about 5 to about 6.

Preferably, the crosslinked carboxymethylcellulose, for example a citric acid crosslinked carboxymethylcellulose, when in the form of particles which are at least 95% by mass in the range of 100 μm to 1000 μm with an average size in the range of 400 to 800 μm and a loss on drying of 10% or less (wt/wt), has a G', media uptake ratio, and tapped density as described below. Such a crosslinked carboxymethylcellulose can be prepared, for example, according to the methods disclosed herein and in US 2016/0354509.

(A) G': at least about 1500 Pa, 1800 Pa, 2000 Pa, 2200 Pa, 2500 Pa, or 2700 Pa. In certain embodiments, the crosslinked carboxymethylcellulose of the invention has a G' when swollen in SGF/water (1:8) of at least about 2800 Pa. In certain embodiments, the crosslinked carboxymethylcellulose of the invention has a G' when swollen in SGF/water (1:8) from about 1800 Pa to about 3000 Pa, about 2000 Pa to about 4000 Pa, from about 2100 Pa to about 3500 Pa, from about 2100 Pa to about 3400 Pa, or from about 2500 Pa to about 3500 Pa.

(B) Media uptake ratio (MUR) in SGF/water (1:8): at least about 40, preferably at least about 50 or 60. In certain embodiments, the crosslinked carboxymethylcellulose has an MUR of about 50 to about 110, about 55 to about 100, about 60 to about 95, about 60 to about 90, or about 60 to about 85.

(C) Tapped density: at least 0.5 g/mL, preferably about 0.55 g/mL to about 0.9 g/mL. In a preferred embodiment, the tapped density is about 0.6 g/mL or greater, for example, from about 0.6 g/mL to about 0.8 g/mL, about 6.5 g/mL to about 7.5 g/mL or about 0.6 g/mL to about 0.7 g/mL.

Preferably, the invention provides a crosslinked carboxymethylcellulose which has a G' and media uptake ratio as set forth below when in the form of particles which are at least 95% by mass in the range of 100 μm to 1000 μm with an average size in the range of 400 to 800 μm and a loss on drying of 10% or less (wt/wt):

(A) G' of about 500 Pa to about 8000 Pa and a media uptake ratio of about 40 to 100;
(B) G' of about 1200 Pa to about 2000 Pa and a media uptake ratio of at least about 75;
(C) G' of about 1400 Pa to about 2500 Pa and a media uptake ratio of at least about 70;
(D) G' of about 1600 Pa to about 3000 Pa and a media uptake ratio of at least about 65;
(E) G' of about 1900 Pa to about 3500 Pa and a media uptake ratio of at least about 60;
(F) G' of about 2200 Pa to about 4000 Pa and a media uptake ratio of at least 55;
(G) G' of about 2600 to about 5000 Pa and a media uptake ratio of at least about 40;
(H) G' above 3000 to about 8,000 Pa and a media uptake ratio of at least about 30;
(I) G' above 4000 to about 10,000 Pa and a media uptake ratio of at least about 20;
(J) G' above 6000 to about 11,000 Pa and a media uptake ratio of at least about 15;
(K) G' above 7,000 to about 12,000 Pa and a media uptake ratio of at least about 10.

Preferably, the foregoing citric acid crosslinked carboxymethylcellulose optionally further has a tapped density of at least 0.5 g/mL, preferably about 0.55 g/mL to about 0.9 g/mL. In a preferred embodiment, the tapped density is about 0.6 g/mL or greater, for example, from about 0.6 g/mL to about 0.8 g/mL, about 0.65 g/mL to about 0.75 g/mL or about 0.6 g/mL to about 0.7 g/mL.

Preferably, the crosslinked carboxymethylcellulose has a G' of at least about 2100 Pa and a media uptake ratio of at least about 75; or a G' of at least about 2700 Pa and a media uptake ratio of at least about 70.

Unless otherwise noted, all measurements of G', MUR and tapped density described herein are made on samples of hydrogel, such as crosslinked carboxymethylcellulose, having (1) a loss on drying of 10% (wt/wt) or less; and (2) are in the form of particulates which are at least 95% by mass in the size range of 100 μm to 1000 μm with an average size in the range of 400 to 800 μm.

Unless otherwise noted, all measurements of G', MUR and tapped density described herein are made on hydrogel samples, including samples of citric acid crosslinked carboxymethylcellulose, having (1) a loss on drying of 15% (wt/wt) or less; and (2) are in the form of particulates which are at least 90% by mass in the size range of 100 μm to 1000 μm with an average size in the range of 400 to 800 μm.

The term "simulated gastric fluid/water (1:8)" and the equivalent term "SGF/water (1:8)", as used herein, refer to a solution prepared according to the method described in Example 2.

As used herein, the "media uptake ratio" or "MUR" of a crosslinked polymer is a measure of the ability of a crosslinked polymer to absorb a specified aqueous medium according to the equation:

$$MUR = (W_{swollen} - W_{dry})/W_{dry}$$

where $W_{dry}$ is the weight of the initial dry crosslinked polymer sample and $W_{swollen}$ is the weight of the crosslinked polymer at equilibrium swelling. Unless otherwise noted, a reference herein to media uptake ratio or MUR refers to the value obtained in SGF/water (1:8) according to the method described in Example 2. It is to be understood that the units for MUR values reported herein are g/g.

As used herein, the "elastic modulus" or G' is determined for a crosslinked polymer swollen in SGF/water (1:8) according to the method described in Example 2.

As used herein, the "tapped density" of a sample is determined according to the method described in Example 2.

As used herein, the "water content" or the "loss on drying" of a sample is determined according to the method described in Example 2.

Preferably, the polymer hydrogels of use in the methods of the invention include cross-linked polymers having G' properties that are stable throughout transit of the polymer in the GI tract, for example, and that also avoid degradation in any portion of the GI tract including in the colon. Alternatively, the preferred hydrogels of the invention may degrade prior to transit through the colon. Alternatively, the preferred hydrogels of the invention may partially degrade during their transit through the GI.

Preferably, the present invention provides a pharmaceutical composition for treating or preventing a gut permeability-related disease or disorder comprising a hydrogel having an elastic modulus (G') of at least about 500 Pa, for example, from about 500 Pa to about 8000 Pa, and preferably a hydrogel comprising a crosslinked carboxymethylcellulose. The pharmaceutical composition can comprise a hydrogel, preferably a hydrogel comprising crosslinked carboxymethylcellulose as an active agent, optionally in combination with a pharmaceutically acceptable excipient or carrier. The hydrogel present in the pharmaceutical composition can be hydrated or dehydrated, for example, with an amount of water less than about 25% by weight. Preferably the pharmaceutical composition is suitable for oral administration. For example, the hydrogel can be dehydrated and formulated as capsules, tablets, or sachets. The hydrogel can also be a component of a formulation or device in which it serves as a mucoadhesive. Such devices include patches in which a layer of the hydrogel is affixed to a barrier layer. Upon adhesion of the hydrogel to the intestinal surface, the patch forms a permeability barrier on the portion of the intestinal wall it covers. See, for example, US 2016/0354509, incorporated herein by reference. The hydrogel can be crosslinked in situ or administered in partially crosslinked form. The hydrogel can be administered in dry (xerogel) or partially swollen or swollen form (hydrogel), alone or in combination with foods or beverages, or a combination thereof. For example, the hydrogel can be mixed with the food or as a component of the food, such as food bars, cereals, yogurts with gel bulks, ice creams, and fruit juices, preferably, but not limited to, beverages with acidic pH, such as orange juice or lemon juice. In another embodiment, the hydrogel is provided in a form which allows it to maintain contact with the oral mucosa, for example, chewable formulations and foods such as popsicles.

The pharmaceutical compositions of the invention can further include pharmaceutically acceptable excipients. In certain embodiments, the pharmaceutical composition is orally administered in combination with water or an aqueous solution. In other embodiments, the composition is administered rectally, for example, as a suppository or in an enema.

Preferably, the hydrogel is administered to the small intestine or colon of a patient by oral ingestion of a dosage form, such as capsule or tablet, in which the hydrogel is coated so as to be released from the dosage form when it reaches the intestinal region where the active disease is prevalent, which varies for Crohn's disease and ulcerative colitis. Thus, typically for an enteric coated capsule, the enteric coating should dissolve in the pH of the jejunum (about pH 5.5), ileum (about pH 6) or colon (about pH 6-7). For example, such a dosage can be achieved by coating the hydrogel, for example in the form of microparticles compressed into a tablet or in a capsule, with a coating that remains intact at the low pH of the stomach, but readily dissolves when the optimum dissolution pH of the particular coating is reached. The coating may be provided on the capsule directly, allowing capsule dissolution only in the GI region of interest. The coating can be selected such that it dissolves at the pH of the target region of the intestines. Hydrogel release can be also modulated by administering a xerogel formulation which swells only under specific environmental conditions, such as pH, ionic strength, and temperature.

Because of the specific backbone stabilization and structure, a delayed release formulation can occur both by diffusion and degradation mechanisms. Molecular diffusion through the bulk can be controlled by network expansion and contraction mechanisms, and degree of cross linking. Expansion and contraction regulate both the steric hindrance of the network 3D structure to the molecule diffusion and the amount of 'free' water (the portion which is not binded nor adsorbed on the backbone) in the hydrogel. High amounts of free water activate convection mechanisms, accelerating molecules permeability and thus release. These mechanisms are controlled by hydrogel swelling and shrinking, which are in turn finely regulated by changes of external GI environment pH and ionic strength. Preferably, the hydrogel swells rapidly under gastrointestinal conditions, for example, within an hour, preferably within 30 minutes or less. The degree of cross linking regulates both network expansion capability and backbone mobility. The higher the expansion and mobility, the lower is the activation energy for molecular diffusion throughout the bulk material. Unexpectedly, high expansion capabilities were obtained at high degree of cross linking, regulating the molecular weight and degree of substitution of the polymer backbone. This adds a powerful tool to control release mechanisms. Additional regulation can be obtained by changing the properties of the polymer backbone, or creating properly designed composite networks.

The compositions disclosed herein are useful for maintaining healthy gut epithelial tissue and in treating or preventing gut permeability-related diseases and disorders in the gut-liver-brain axis. Such diseases and disorders include GI inflammatory diseases and disorders such as, but not limited to: gastritis, peptic ulcer, duodenal ulcer, gastroesophageal reflux disease (GERD), acid reflux, eosinophilic esophagitis, inflammatory bowel disease (IBD), including Crohn's diseases and ulcerative colitis, food allergies, irritable bowel syndrome (IBS), celiac disease, NSAID-induced ulcers, infectious colitis, infection or trauma to the gastrointestinal tract including infection by *H. pylori; Salmonella* spp., including *Salmonella enterica serovar typhimur; Shigella; Staphylococcus; Campylobacter; Clostridium difficile*; pathogenic *Escherichia coli; Yersinia; Vibrio* spp, including *V. cholera* and *V. parahaemolyticus; Candida; Giardia; Entamoeba histolytica, Bacteroides fragilis*; rotavirus; norovirus; adenovirus; and astrovirus; inflammation in the gastrointestinal tract, gut acute radiation syndrome, food allergies; environmental enteropathy and mucositis, such as chemotherapy- or radiotherapy induced oral or intestinal mucositis; colorectal cancer both colitis associated and sporadic. Such diseases and disorders further include metabolic diseases and diseases affecting tissues and organs outside the gastrointestinal tract, including obesity, mixed connective tissue disease (MCTD); chronic inflammation, including arthritis; acute inflammation, including sepsis; liver disease, including non-alcoholic steatohepatitis (NASH) and non-alcoholic fatty liver disease (NAFLD), cirrhosis and hepatocellular carcinoma; Type 1 diabetes mellitus; Type II diabetes mellitus; sequelae of chronic alcoholism; infections, including respiratory infections; neurological disorders such as autism spectrum disorders, Alzheimer and Parkinson's Disease.

The compositions disclosed herein are also useful in prophylactically preventing injury to gut epithelial tissues resulting from side effects of various pharmacological therapies that may be administered to a patient. For example, Compositions of the present invention may be used as a maintenance and prevention after or during the treatment with pharmacological therapy.

Compositions of the present invention may be used alone or in combination with other pharmacological therapies and active therapeutic drug agents. They may be used to improve the efficacy of a pharmacological treatment for diseases related to gut permeability and or to help reducing the negative effects of such treatments by reducing the required doses and or treatment period of such treatments. As used herein the terms "combination therapies", "co-therapeutic treatment regimens" and the like mean treatment regimens wherein two drugs are administered simultaneously, in either separate or combined formulations, or sequentially at different times separated by minutes, hours or days, but in some way act together to provide the desired therapeutic response. Any known pharmacological therapies for the treating the particular disease (e.g. a disease related to gut permeability) may be used in accordance with the invention.

Compositions of the present invention may be used as a vehicle to deliver pharmacological therapies. When used as a drug delivery tool, they play the multiple role of both increasing drug availability and contact time and providing a therapeutic effect through protecting and stimulating the epithelial tissue, improving regeneration and preventing inflammation. From this perspective, hydrogels of the present invention are not just an additional tool to drug administration but provide a synergistic effect to gut permeability related pathologies. This could be beneficial during and the treatment period and also for protecting and for maintenance of gut health after such treatment. A combination therapy as such may provide an improved efficacy and safety profile to the overall therapy, and or just an improved convenience and life quality.

Drug delivery can be modulated both in cases of non-dissolving, partially dissolving or completely dissolving hydrogels. In non-dissolving hydrogels, drug delivery can be modulated acting on the molecular weight, the degree of crosslinking of the backbone, the presence of fixed charges and their degree of substitution. These affect directly the hindrance to the molecular transport inside the hydrogel, and its swelling properties, which in turn modulate diffusion kinetic as well.

Without being bound by theory, and just as an example, hydrogel with higher degree of crosslinking and higher molecular weight display higher hindrance to molecular transport and lower mobility, also reducing transport kinetic. Lower swelling capacity also reduces transport mechanism, thus reducing the delivery kinetic. In polyelectrolytes, swelling capacity, and thus delivery kinetics, may also be regulated by the properties of external media, such as pH and ionic strength. This allows to properly target the specific GI tract site of drug delivery. Combination of polyelectrolytes and non-polyelectrolytes-based networks provides further control of transport phenomena, and thus delivery mechanisms, through the above-mentioned mechanisms.

Such combinations may also promote partial or complete hydrogel degradation, as described in this application. This degradation can be used as an additional tool for the modulation of the delivery properties. In fact, the degradation (partial or complete) of the backbone activates the release of the drug present in the degrading hydrogel mass. In turn, this degradation may be activated by external environment modifications or by external tools, properly controlling the GI delivery sections and amounts of drug to be delivered.

Another tool to control the precise site of delivery is the proper selection of charges on the polyelectrolyte. In fact, it is known that inflamed tissues strongly interact with charged backbones. Polyelectrolytes-based hydrogels of this invention can bind to inflamed tissues sections and both target the delivery site and improve drug availability on these sites.

Drug delivery control may be also enhanced by drug encapsulation in microspheres or microcapsules, which in turn are incorporated in the hydrogel and either dissolved or destroyed by contact with external media or external tools, such as ultrasounds, local temperature modifications, radiations, etc. Their controlled dissolution releases the drug which has been previously encapsulated either in the capsule or in the shell of two or more concentric capsules. Hydrogel backbone and capsule combination may occur by simple mixing, secondary or primary bonding.

Coupling regeneration mechanisms to target drug delivery mechanism plays an important rule on a number of diseases where drug administration alone has issues of safety and efficacy. An example, without any limitation to this case, is the administration of chemotherapy agents, known to be associated to intestinal tissues inflammation.

NAFLD/NASH therapeutic candidates that could be synergistic via its effect on gut barrier or could add a different mechanism to approach the disease or added to the hydrogel could provide a sustained or slow release mode of administration include FHX agonists, bile acid uptake inhibitor, Antioxidant (Mitoquinone, cysteine depleting agent), PPAR agonists (single and dual), Caspaseprotease inhibitor, Fibroblast Growth Factor Analog (FGF 19 or FGF 21). Sirtuin stimulant, fatty acids inhibitor, DGAT1 inhibitor, ROCK2 inhibitor, ASK1 inhibitor, TLR-4 antagonist, THR-beta agonist, Apoptosis Signal Reducing Kinase-1 Inhibitor, Cholesterol Biosynthesis Inhibitor/IL-6 modulator, Stearoyl Coenzyme A Desaturase 1 Inhibitor, Chemokine Receptor Type 2 and 5 Inhibitor, Cathepsin B inhibitor, Acetyl-CoA Carboxylase Inhibitor, and galectin 1 and 3 inhibitors.

Using hydrogel for peptide delivery would allow oral administration of the following treatment LOXL2 antibody, GLP-1 agonist, GLP-2 agonist, galectin 1 and 3 inhibitors.

Inflammatory bowel disease therapeutic candidates that could be synergistic via its effect on gut barrier or could add a different mechanism to approach the disease or added to the hydrogel could provide a sustained or slow release mode of administration include mesalanine, azathioprine, 6-mercaptopurine, methotrexate, corticosteroids, Anti-tumor necrosis factor (TNF) drugs (infliximab, adalimumab, certolizumab pegol, infliximab, adalimumab, and golimumab), anti-alpha-4 beta-7 integrin antibody (vedolizumab, Etrolizumab), Sphingosine-1-phosphate (S1P1) receptor modulators (ozanimod), anti-P40 antibody (Ustekinumab), anti-IL-23 antibodies, anti-P19 antibody, Janus kinase (JAK) inhibitors (Tofacitinib, filgotinib), metalloproteinase-9 antibody, SMAD7 antisense oligonucleotide (mongerse).

Irritable bowel syndrome (constipation predominant) therapeutic candidates that could be synergistic via its effect on gut barrier or could add a different mechanism to approach the disease or added to the hydrogel could provide a sustained or slow release mode of administration include polyethylene glycol substances; guanylate cyclase-C agonists (linaclotide, plecanatide), chloride channel activator (lubiprostone), sodium/hydrogen exchanger inhibitor (tenapanor). For IBS (where diarrhea is predominant) neurokinin-2 receptor antagonist (ibodutant), histamine H1-receptor antagonist (ebastine), FXR-agonists could be additive or synergistic to the hydrogel. Agents like Eluxadoline and 5-HT3 antagonist added to the hydrogel could allow use of lower doses and reducing risk of pancreatitis in IBS-D.

Preferably the invention provides combination therapies involving the hydrogels of the invention in combination with drugs or foods or food supplements having a mechanism of action that involves changing, managing or effecting the microbiota of the gut. For example, very large amounts of inulin or other soluble fibers may be administered to a patient to effect positive changes in the microbiome and the related metabolites. However, since many of these soluble fibers have very poor mechanical properties large doses are required to be effective and such large doses may cause undesirable side effects. The combination of the hydrogels of the invention with these soluble fibers may increase efficacy while allowing lower doses to be delivered via multiple mechanisms, mechanical and chemical that together effect the microbiota to provide improved therapy.

A pharmaceutical composition in accordance with the invention is administered to the subject following a therapeutically effective regimen, for length of time resulting in an improvement in one or more symptoms. For example, one or more compositions of the invention may be administered at least once a day, at least twice every day, at least three times every day or more. The subject is treated for a length of time effective to reduce one or more symptoms associated with the disease or disorder, for example, the severity of inflammation, the extent of inflammation, pain and so forth. For example, the subject can be treated for 1 week, 2 weeks, 3 weeks, 4 weeks, 5 weeks, 6 weeks, 7 weeks, 8 weeks, 9 weeks or 10 weeks. The compositions can be administered alone or in combination with other bioactive agents.

Therefore, the invention provides a method for treating or preventing a gut permeability- and/or inflammation-related disease or disorder with or without dysbiosis (i.e. a condition related to an unbalance of the intestinal mutualistic microflora (microbiota)) in a subject in need thereof, comprising administering to the gastrointestinal tract of the subject a therapeutically effective amount of a hydrogel, preferably a hydrogel having an elastic modulus (G') of at least about 500 Pa, for example, from about 500 Pa to about 8,000 Pa and preferably from about 500 Pa to about 10,000 Pa, as is described above. Preferably the hydrogel is orally administered to the subject. The disease or disorder can be limited to the gastrointestinal tract, manifest in tissue(s) or organ(s) outside the gastrointestinal tract or systemic. Such diseases and disorders include GI inflammatory diseases and disorders with or without dysbiosis such as, but not limited to: gastritis, peptic ulcer, duodenal ulcer, gastroesophageal reflux disease (GERD), acid reflux, eosinophilic esophagitis, inflammatory bowel disease (IBD), including Crohn's diseases and ulcerative colitis, celiac disease, NSAID-induced ulcers, food allergies, irritable bowel syndrome (IBS), infectious colitis, infection or trauma to the gastrointestinal tract including infection by *H. pylori; Salmonella* spp., including *Salmonella enterica serovar typhimur; Shigella; Staphylococcus; Campylobacter; Clostridium difficile*; pathogenic *Escherichia coli; Yersinia; Vibrio* spp, including *V. cholera* and *V. parahaemolyticus; Candida; Giardia; Entamoeba histolytica, Bacteroides fragilis*; rotavirus; norovirus; adenovirus; and astrovirus; inflammation in the gastrointestinal tract, gut acute radiation syndrome, food allergies; environmental enteropathy and mucositis, including chemotherapy and radiotherapy-induced oral and intestinal mucositis; dysbiosis; colorectal cancer both colitis associated and sporadic. Such diseases and disorders further include diseases and tissues affecting tissues and organs outside the gastrointestinal tract, including mixed connective tissue disease (MCTD); chronic inflammation, including arthritis; acute inflammation, including sepsis; liver diseases, including non-alcoholic steatohepatitis (NASH) and non-alcoholic fatty liver disease (NAFLD), cirrhosis and hepatocellular carcinoma; Type 1 diabetes mellitus; Type II diabetes mellitus; sequelae of chronic alcoholism; infections, including respiratory infections; neurological disorders such as autism spectrum disorders, Alzheimer's and Parkinson's Disease. Preferably the hydrogel comprises citric acid crosslinked carboxymethylcellulose.

Preferably the composition is administered in a dosage form suitable for oral administration comprising a hydrogel, preferably a hydrogel having an elastic modulus (G') of at least 500 Pa, for example from about 500 Pa to about 8,000 Pa and preferably from about 500 Pa to about 10,000 Pa or from about 500 Pa to about 6500 Pa.

Pharmaceutical compositions of the invention are also suitable for use in methods of promoting regeneration of mucosa to restore physiological structure and function to the damaged or dysfunctional mucosa resulting from a disease or disorder. Mucosal regeneration and tight junctions are responsible for a better barrier to molecular traffic in the intestine and thus reduced inflammation of the tissues underneath. This has an impact on the treatment of gut permeability- and/or inflammation or dysbiosis-related diseases and disorders, such as those described above. Therefore, the invention provides methods for treating a gut permeability- and/or inflammation or dysbiosis-related disease or disorder comprising the step of contacting a hydrogel, preferably a hydrogel having an elastic modulus (G') of at least about 500 Pa, for example, from about 500 Pa to about 10,000 Pa, with intestinal tissue in need of repair or regeneration.

Pharmaceutical compositions and methods of the invention are also suitable in methods for promoting the formation of tight junctions between epithelial cells of the mucosa of the GI tract. Healthy, mature gut mucosa with its intact tight junction serves as the main barrier to the passage of macromolecules. Therefore, the invention also provides methods of promoting the formation of tight junctions of the gastrointestinal (GI) tract comprising the step of contacting a hydrogel, preferably a hydrogel, preferably a hydrogel having an elastic modulus (G') of about 500 Pa to about 8,000 Pa and preferably from about 500 Pa to about 0,000 Pa, with the region or regions of the intestinal tract having disturbed permeability.

The hydrogel of the invention does not necessarily need to directly contact the intestinal wall at a site of impaired permeability but may simply increase the elasticity of the transient luminal volume and/or epithelial associated mucus layer. Contact of the intestinal wall with the elastic gel or gel-enhanced luminal contents promotes regeneration of the gut barrier, or in addition prevents or inhibits the disruption of the barrier by aggression of external media and by inducing reconstitution of the luminal mucus layer. Without being bound by theory, it is believed that the hydrogel acts as a scaffold matching the range of mechanical properties of the underlying tissue or mucus, thus providing mechanosensing signals to underlying, and sustains tissue regeneration. The hydrogel does not prevent the nutrient transport necessary for regeneration of the underlying tissue because of its permeability and similarity of mechanical properties with those of the regenerating tissue and/or mucus.

In particular, it is believed that when present in the intestinal lumen, the hydrogel promotes cell-biomaterial interactions, cell adhesions, sufficient transport of gases, nutrients and regulatory factors for cell survival, proliferation and differentiation without provoking or increasing inflammation of tissue of the intestinal lumen as compared to the amount of inflammation in the intestinal lumen prior to contacting the intestinal lumen with the hydrogel.

Therefore the invention further provides a method of forming a temporary scaffold in the GI tract comprising contacting the GI tract with a hydrogel, preferably a hydrogel having an elastic modulus (G') of at least about 500 Pa, for example, from about 500 Pa to about 10,000 Pa wherein the hydrogel forms a scaffold in the GI tract wherein the scaffold promotes cell-biomaterial interactions, cell adhesions, sufficient transport of gases, nutrients and regulatory factors for cell survival, proliferation and differentiation or any combination thereof wherein the temporary scaffold does not increase inflammation of the GI tract as compared to the amount of inflammation in the intestinal lumen prior to contacting the GI tract with the hydrogel.

The present invention can be further understood in view of the following non-limiting examples.

EXAMPLES

Example 1—Methods for Making GelB-01, GelB-02, GelB-03 and GelB-04

Polymers according to Table 1 were prepared as set forth in Example 1 of US 2016/0222134, except that for GelB-03 and GelB-04, the crosslinking time was increased as indicated in the Table 1.

TABLE 1

| Name | X-link Time (time@120° C.) | MUR | Average MUR | G' [Pa] | Average G' [Pa] |
|---|---|---|---|---|---|
| Gel B-01 | Not X-linked | | | | |
| Gel B-02 | 4 hours | 78, 76, 77 | 77 | 1966, 1885, 1688 | 1827 |
| Gel B-03 | 6 hours | 36, 36, 36 | 36 | 5358, 5064, 5227 | 5293 |
| Gel B-04 | 8 hours | 24, 25, 21 | 23 | 6880, 7757 | 7319 |

Gel B-01, Gel B-02, Gel B-03 and Gel B-04 Were Prepared as Follows.

For the mixing step, a homogeneous mixture of citric acid (0.2% w/w CMCNa), 7H4MF (6% w/w DI Water) carboxymethyl cellulose and DI water was obtained through planetary mixer technology. Three (3) hours of mixing were enough to prevent any lumps in the mixture. For the drying step, a thin layer of CA/CMC/Water mixture was rolled out on a silicone sheet. The homogeneity of the layer is important to promote homogeneous drying and to prevent any residual stress in the material. The drying temperature was 70° C. For the first milling step, the dried material was ground by a cutting mill through 2 mm screen. For the first sieving, the ground material was sieved between 100-1600 microns. The material obtained at this step is labelled Gel B-01. For the crosslinking step, 5 g of powder with a selected particle size of 100-1600 microns was placed in aluminum dishes and crosslinked at 120° C. for 4 hours. The material obtained at this step is labelled Gel B-02. Five (5) grams of Gel B-02 was further crosslinked in aluminum dishes at 120° C. for 2 and 4 extra hours to give Gel B-03 and Gel B-04 respectively. For the washing and drying step, the crosslinked powder was washed in DI water for 3 hours under constant stirring and then filtered and dried at 70° C. For the second milling step, the dried crosslinked material was ground by a cutting mill through 1 mm screen. For the second sieving step, the ground material was sieved for the final selected particle size of 100-1000 microns. The elasticity (G') when swollen in SGF/water (1:8) of each of Gel B-01, Gel B-02 Gel B-03 and Gel B-04 are found in Table 1.

Gel A Was Prepared as Follows.

For the mixing step, a homogeneous mixture of citric acid (0.3% w/w CMCNa), 7H3 SXF (6% w/w DI Water) carboxymethyl cellulose and DI water was obtained through planetary mixer technology. Three (3) hours of mixing were enough to prevent any lumps in the mixture. For the drying step, a thin layer of CA/CMC/Water mixture was rolled out on a silicone sheet. The homogeneity of the layer is important to promote homogeneous drying and to prevent any residual stress in the material. The drying temperature was 70° C. For the first milling step, the dried material was ground using a cutting mill through 2 mm screen. For the first sieving step, the ground material was sieved to between 100-1600 microns. For the first crosslinking step, 5 g of powder with a selected particle size of 100-1600 microns were placed in aluminum dishes and crosslinked at 120° C. for 8 hours. For the washing and drying step, the crosslinked powder was washed in DI hour for 3 hours under constant stirring and then filtered and dried at 70° C. For the second milling step, the dried crosslinked material was ground using a cutting mill through a 1 mm screen. For the second sieving step, the ground material was sieved for the final selected particle size 100-1000 microns; The material obtained at this step is labelled as Gel A. The elasticity (G') when swollen in SGF/water (1:8) of Gel A, is found in Table 2.

Gels C and D Were Prepared as Follows.

Gel C and Gel D were obtained by dissolving NaCMC 7H3 and 7H4 respectively in distilled water to form a homogeneous solution containing about 6 percent of polymer by weight based on total solution weight (Solution A). Poly(ethylene glycol) diglycidyl ether (PEGDE) was dissolved in water to form a solution containing 1 percent of PEGDE by weight based on total solution weight (Solution B). Sodium hydroxide was dissolved in water to form a stock solution containing 4 percent of NaOH (1M) by weight based on total solution weight (Solution C). Solution B (crosslinker) was added to the Solution A to provide a solution with the desired ratio of polymer and PEGDE. In formulations with a catalyst, an amount of solution C was added to the solution of polymer and PEGDE to yield a hydroxide concentration in the final solution of 0.25M. The resulting solution consisting of NaCMC, PEGDE (and optional NaOH in formulations with a catalyst) was mixed for at least three hours to make it homogenous. The mixture was cast by evaporative drying at 50° C. in an air-convection oven for 48 hours.

After drying, the recovered cross-linked carboxymethylcellulose was ground into granules in a blender. The ground material was sieved and the fraction between 100 and 1000 mm and was collected and used for next steps.

The polymer/PEGDE dry mix (with or without a catalyst) was treated at 120° C. for 4 hours in an oven to complete cross-linking reaction, where necessary, in order to improve mechanical properties. The cross-linked carboxymethylcellulose (glucomannan or a mixture of them) reacted with PEGDE and NaOH as the catalyst was washed with acidic water (0.25M hydrochloric acid) from 1 to 3 hours in order to remove unreacted materials and byproducts and to neutralize catalyst by restoring pH to 7. The crosslinked carboxymethylcellulose reacted with the PEGDE without a catalyst was washed with distilled water from 1 to 3 hours to remove unreacted materials and byproducts.

The material obtained after drying was ground and sieved between 500 and 1000 microns. The final material obtained at this step is labelled as Gel C or Gel D (based product respectively by 7H3 on 7H4). The elasticity (G') when swollen in SGF/water (1:8) of Gels C and D, is found in Table 2.

PEGDA 5%, 10% and 15% Gels Were Prepared as Follows.

PEGDA (Sigma-Aldrich, 700 Da) was dissolved in distilled water (5%, 10% and 15% w/v), by gentle mixing to obtain PEGDA 5%, PEGDA 10% and PEGDA 15% samples. The photoinitiator Darocur 1173 (Bast) was added in a 3% w/w amount with respect to the PEGDA content.

Solutions were cast in Petri dishes (1.5 ml in a 35 mm dish) and frozen under controlled conditions (−40° C., freezing rate—1° C./min) in a freeze-dryer (Virtis Advantage). After holding at −40° C. for 1 h, samples were exposed to UV light (365 nm, 2 mW/cm^2) for 30 s or 60 s, and finally swollen in distilled water, for the removal of ice crystals and unreacted precursors. The materials were then dried at 50° C. for 24 h. The obtained samples were then ground to obtain 100-1000 microns particles. The elasticity (G') when swollen in SGF/water (1:8) of each respective PEGDA gel, is found in Table 2.

FIBER A (Psyllium METAMUCIL) Gel Description.

Metamucil is a brand of fiber supplements containing psyllium fiber for multiple benefits. Psyllium is an ingredient of natural fiber from *Plantago ovata*. The elasticity (G') when swollen in SGF/water (1:8) of FIBER A, is found in Table 2.

FIBER B (Microcrystalline Cellulose (AVICEL) Gel Description.

AVICEL cellulose gel is a network of gels formed with colloidal microcrystalline cellulose (MCC). It is transformed from special qualities of renewable hardwood and softwood pulp. The elasticity (G') when swollen in SGF/water (1:8) of FIBER B, is found in Table 2.

FIBER C (Glucomannan) GEL Description.

Glucomannan is a vegetable dietary fiber extracted from the Konjac plant. This fiber has already been known for many years in Japan for its health benefits. The elasticity (G') when swollen in SGF/water (1:8) of FIBER C, is found in Table 2.

FIBER D (Guar Gum) Gel Description.

Guar gum is a product that can form a hydrocolloid. It is obtained by grinding the endosperm of the seeds of the guar *Cyamopsis tetragonoloba*, a herbaceous plant of legumes typical of India and Pakistan, whose seeds are used locally for food for centuries. The main constituent is a galactomannan, a trisaccharide formed by units of mannose and galactose, specifically polymerized to form α-D-mannopyranosyl chains combined with a β-D-(1-4) glycosidic bond and of molecular weight around 200,000-300,000 daltons, to form a linear chain 1-4 with short lateral branches 1-6 of galactose. The elasticity (G') when swollen in SGF/water (1:8) of FIBER D, is found in Table 2.

TABLE 2

| Hydrogel/Fiber Name | Description | Elasticity (Pa) in 1:8 SGF:Water |
|---|---|---|
| Gel A | CMC(LV*)/CA-hydrogel | 1298 |
| Gel C | CMC(LV*)/PEGDE-hydrogel | 941 |
| Gel D | CMC(HV**)/PEGDE-hydrogel | 2,254 |
| PEG 5% | PEGDA-Crosslinked hydrogel - 5% concentration | 380 |
| PEG 10% | PEGDA-Crosslinked hydrogel - 10% concentration | 2,000 |
| PEG 15% | PEGDA-Crosslinked hydrogel - 15% concentration | 5,500 |
| FIBER A | Psyllium | 77 |
| FIBER B | Microcrystalline Cellulose | NA (insoluble) |

TABLE 2-continued

| Hydrogel/Fiber Name | Description | Elasticity (Pa) in 1:8 SGF:Water |
|---|---|---|
| FIBER C | Glucomannan | 570 |
| FIBER D | Guar Gum | 236 |

*LV - Low Viscosity CMC (7H3)
**HV - Low Viscosity CMC (7H4)

Example 2—Materials and Methods for Characterizing Hydrogels of the Invention Using Carboxymethylcellulose (CMC) as an Example Preparation of Simulated Gastric Fluid/Water (1:8)

Reagents used for preparation of SGF/water (1:8) solution are purified water, sodium chloride, 1M hydrochloric acid and pepsin.

1. To a 1 L graduated cylinder pour about 880 mL of water.
2. Place the cylinder on a magnetic stirrer, add a magnetic bar and start stirring.
3. Begin monitoring the pH of the water with a pH meter.
4. Add a sufficient amount of 1M hydrochloric acid to bring the pH to 2.1±0.1.
5. Add 0.2 g NaCl and 0.32 g pepsin. Leave the solution to stir until complete dissolution.
6. Remove the magnetic bar and the electrode from the cylinder.
7. Add the amount of water required to bring the volume to 900 mL.

Determination of Viscosity of Carboxymethylcellulose Solutions

Equipment and Materials:

Constant temperature water bath.

Glass Bottle, 500 ml with a cap, diameter of the neck at least 80 mm.

Brookfield Viscometer, model Myr VR3000 (ECO208) or equivalent equipped with: Spindle L4.

Thermal printer (PRP-058GI).

Mechanical overhead stirrer with anchor stainless steel stirrer.

Chain clamp to secure glassware.

Lab spatula.

Aluminum crucible.

Analytical balance, capable of weighing to the nearest 0.001 g.

Calibrated balance, capable of weighing, to the nearest 0.1 g.

Purified water.

Preparation of Test Samples:

Prepare three CMC/water solutions as described below:

1. Measure the moisture content of CMC powder as described in [B] below.
2. Calculate the amount of water required using the equation:

$$\text{water required [g]} = 3 \times (99 - \text{LOD}_{average}).$$

3. Weigh the needed amount of water for preparing the CMC solution into a beaker.
4. Pour roughly half of this water into the bottle, with the rest of the water remaining in the beaker.
5. Place and tie up the bottle under the stirrer motor with a chain clamp.
6. Insert the stirrer.
7. Mix the sample to assure uniformity.
8. Weigh 3.0±0.1 g of CMC powder.

9. Pour the powder in small amounts into the bottle while mixing at low speed (ca. 600 rpm).

10. Mix for 2 minutes and set the mixing speed to 1000 rpm.

11. Mix for no less than 10 minutes but no more than 30 minutes.

12. Add the remaining water.

13. Mix for additional 30 minutes.

14. If the CMC is not dissolved completely, continue stirring.

15. Once all the CMC is dissolved remove the anchor stainless steel stirrer and place the cap on the bottle.

16. Place the flask in the constant temperature bath, at 25.0° C.±0.1° C., for at least 30 minutes but no longer than one hour.

17. Shake the bottle vigorously for 10 seconds. The solution is ready to be tested.

Viscosity Measurement:

1. Determine viscosity of each sample according to the instructions for the viscometer. Allow rotation of spindle for exactly 3 minutes.

2. Determine the average viscosity of the three solutions.

Determination of Loss on Drying

The moisture content of a carboxymethylcellulose or crosslinked carboxymethylcellulose is determined according to USP <731>, Loss on Drying.

Instruments/Equipment

Moisture Analyzer Radwag, Model WPS 50S

Lab Spatula

Aluminum crucible

Desiccator with silica gel

Procedure

1. Place the sample in the desiccator for at least 12 hours.

2. Place the aluminum crucible on the scale pan of the moisture analyzer and tare the balance.

3. Accurately weigh 1.000±0.005 g of a sample in the aluminum crucible. The initial weight of the sample is $W_i$.

4. Set the Moisture Analyzer to heat the sample at 105° C. for 30 minutes under ambient pressure and moisture.

5. Turn on the Moisture Analyzer and run the LOD program (30 min at 105° C.).

6. Weigh the sample. The final weight of the sample is $W_f$.

The LOD value is determined according to the equation:

$$LOD = (W_i - W_f)/W_i \times 100\%.$$

The Loss on Drying is determined in triplicate, and the reported LOD is the average of the three values.

Determination of Particle Size Range

Equipment and Materials:

Sieve Shaker Retsch, Model AS 200 basic

Stainless Steel Sieves with mesh sizes 1000 µm and 100 µm

Aluminum weighing pan

Laboratory stainless steel spatula

Calibrated balance, capable of weighing to the nearest 0.1 g.

Procedure:

1. Weigh the empty sieves and the aluminum pan to the nearest 0.1 g.

2. Weigh out 40.0±0.1 g of powder.

3. Stack the test sieves with sizes 1000 and 100 µm with larger pore size on the top and the smaller at the bottom. Assemble the aluminum pan at the bottom of the nest.

4. Pour the sample into the 1000 µm sieve, at the top of the stack.

5. Place this stack between the cover and the end pan of the shaker, so that the sample remains in the assembly.

6. Turn on the main switch of the shaker.

7. Set knob UV2 of the shaker for continuous operation.

8. Turn the knob MN2 of the shaker to the right to increase the vibration height until 50.

9. Shake this stack with the shaker for 5 minutes.

10. Disassemble the sieve and reweigh each sieve.

11. Determine the percentage weight of test specimen in each sieve as described in paragraph 8.

12. After measuring the weight of the full and empty test sieves, determine, by difference, the weight of the material inside each sieve.

13. Determine the weight of material in the collecting pan in a similar manner.

14. Use the weight of sample contained in each sieve and in the collecting pan to calculate the % distribution with the following equation:

$$Wx\% = Wx/Wsample * 100\%$$

where:

Wx %=sample weight in each sieve or in the collecting pan, in percentage where the index "x" is:

">1000" for particle size bigger than 1000 µm.

"100-1000" for particle size between 100 and 1000 µm.

"<100" for particle size smaller than 100 µm.

Wsample=initial weight of test specimen.

Determination of Tapped Density

Equipment and materials:

100 mL glass graduated cylinder 100 mL glass beaker

Lab spatula

Mechanical tapped density tester, Model JV 1000 by Copley Scientific

Calibrated balance capable of weighing to the nearest 0.1 g.

Procedure:

1. Weigh out 40.0±0.1 grams of test sample. This value is designated M.

2. Introduce the sample into a dry 100 mL glass graduated cylinder.

3. Carefully level the powder without compacting and read the unsettled apparent volume, V0, to the nearest graduated unit.

4. Set the mechanical tapped density tester to tap the cylinder 500 times initially and measure the tapped volume, V500, to the nearest graduated unit.

5. Repeat the tapping 750 times and measure the tapped volume, V750, to the nearest graduated unit.

6. If the difference between the two volumes is less than 2%, V750 is the final tapped volume, Vf, otherwise repeat in increments of 1250 taps, as needed, until the difference between succeeding measurements is less than 2%.

Determination of Elastic Modulus (G')

The elastic modulus (G') is determined according to the protocol set forth below. The rheometer used is a Rheometer Discovery HR-1 (5332-0277 DHR-1) by TA Instruments or equivalent, equipped with a Peltier Plate; a Lower Flat plate Xhatch, 40 mm diameter; and an Upper Flat plate Xhatch, 40 mm diameter.

Procedure

1. Put a magnetic stir bar in a 100 mL beaker.

2. Add 40.0±1.0 g of SGF/Water (1:8) solution prepared as described above to the beaker.

3. Place the beaker on the magnetic stirrer and stir gently at room temperature.

4. Accurately weigh 0.250±0.005 g of crosslinked polymer (e.g. carboxymethylcellulose) powder using a weighing paper ($W_{in}$).

5. Add the powder to the beaker and stir gently for 30±2 min with the magnetic stirrer without generating vortices.
6. Remove the stir bar from the resulting suspension, place the funnel on a support and pour the suspension into the funnel, collecting any remaining material with a spatula.
7. Allow the material to drain for 10±1 min.
8. Collect the resulting material.
9. Subject the material to a sweep frequency test with the rheometer and determine the G' value at an angular frequency of 10 rad/s.

The determination is made in triplicate. The reported G' value is the average of the three determinations.

Determination of Media Uptake Ratio (MUR) in SGF/Water (1:8)

The media uptake ratio of a crosslinked carboxymethylcellulose in SGF/water (1:8) is determined according to the following protocol.

1. Place a dried fritted glass funnel on a support and pour 40.0±1.0 g of purified water into the funnel.
2. Wait until no droplets are detected in the neck of the funnel (about 5 minutes) and dry the tip of the funnel with an absorbent paper.
3. Place the funnel into an empty and dry glass beaker (beaker #1), place them on a tared scale and record the weight of the empty apparatus ($W_{tare}$).
4. Put a magnetic stir bar in a 100 mL beaker (beaker #2); place beaker #2 on the scale and tare.
5. Add 40.0±1.0 g of SGF/Water (1:8) solution prepared as described above to beaker #2.
6. Place beaker #2 on the magnetic stirrer and stir gently at room temperature.
7. Accurately weigh 0.250±0.005 g of crosslinked carboxymethylcellulose powder using a weighing paper ($W_{in}$).
8. Add the powder to beaker #2 and stir gently for 30±2 min with the magnetic stirrer without generating vortices.
9. Remove the stir bar from the resulting suspension, place the funnel on a support and pour the suspension into the funnel, collecting any remaining material with a spatula.
10. Allow the material to drain for 10±1 min.
11. Place the funnel containing the drained material inside beaker #1 and weigh it ($W'_{fin}$).

The Media Uptake Ratio (MUR) is calculated according to:

$$MUR = (W_{fin} - W_{in})/W_{in}.$$

$W_{fin}$ is the weight of the swollen hydrogel calculated as follows:

$$W_{fin} = W'_{fin} - W_{tare}.$$

wherein $W_{in}$ is the weight of the initial dry sample. The MUR is determined in triplicate for each sample of crosslinked carboxymethylcellulose and the reported MUR is the average of the three determinations.

Example 3—Animal Studies

C57BL6/J mice were purchased from Charles River Laboratories. All mice used were between 8 to 12 weeks of age at the time of the experiment. Mice were maintained at IFOM-IEO Campus animal facility under specific pathogen-free conditions. All experiments were performed in accordance with the guidelines established in the Principles of Laboratory Animal Care (directive 86/609/EEC).

C57BL6/J female and male mice at 8 weeks of age were fed with chow diet supplemented with different concentrations of Gel B-02 (2%-4%-6%-8%) and the respective control chow diet (4RF21 repelletted, Mucedola srl) for 4 weeks. The description of Gel B-02 is found in Table 1 of Example 1.

After 4 weeks of feeding mice were morning fasted for 6 hours and blood samples were collected from the tail vein through a small cut with a sharp scalpel. A drop of blood was directly used to measure glucose levels using a hand-held whole-blood glucose monitor from Roche (Accu-Chek Aviva, Roche), and other 50 µL of blood were collected to obtain sera to measure insulin levels by ELISA (Mouse Ultrasensitive Insulin ELISA, Mercodia AB).

During the 4 weeks, mice were weighted and monitored for food and water intake and stools samples were collected and weighted. At the end of the 4 weeks, mice were sacrificed. Blood was collected from the heart to obtain sera and liver, epididimal/inguinal white adipose tissue, interscapular brown adipose tissue, small and large intestine were collected from each mouse. Different segments of the intestine were fixed in paraformaldehyde, L-Lysine pH 7.4 and $NaIO_4$ (PLP Buffer) or in Carnoy's fixative. Livers were fixed in PLP Buffer or in paraformaldehyde and brown and white adipose tissues were fixed in paraformaldehyde.

All mice used were between 8 to 12 weeks of age at the time of the experiment. Mice were maintained at IFOM-IEO Campus animal facility under specific pathogen-free conditions. All experiments were performed in accordance with the guidelines established in the Principles of Laboratory Animal Care (directive 86/609/EEC).

Carnoy's Fixation and Mucus Staining

To preserve mucus layer, tissues were fixed in Carnoy's fixative (Ethanol, Acetic Acid Glacial, Chloroform 6:1:3). After 40 minutes (ex vivo organ culture) or 2 hours (in vivo experiments) of fixation tissues were transferred in absolute ethanol and kept at +4° C. for at least 72 hours, processed and paraffin embedded.

Tissues were then stained using Alcian Blue-PAS ready to use staining kit (NOVAULTRA™ Alcian Blue/PAS Stain Kit, IHC WORLD) following provider's instructions. Alcian blue will stain strongly acidic mucins in blue, PAS (Periodic Acid Solution and Schiff Reagent) will stain neutral mucins in magenta. Mixtures of both acidic and neutral mucins will be stained blue purple.

Immunohistochemistry for Ki67 was performed on Carnoy's fixed paraffin-embedded tissues. Tissue sections were deparaffinized in histolemon and hydrated through graded alcohol series. Antigen unmasking was performed using Tris-EDTA pH 9 at 95° C. for 50 minutes, followed by quenching of endogenous peroxidases using 3% $H_2O_2$.

Sections were then incubated with primary rabbit polyclonal antibody against Ki67 (ab15580, ABCAM) for 2 hours at room temperature and with secondary antibody ready to use (DAKO Envision system HRP rabbit) for 20 minutes at room temperature. Tissue sections were then washed and incubated with peroxidase (DAB, DAKO) solution. Slides were then counterstained with hematoxilyn and dehydrated through graded alcohol series, washed in histolemon and mounted. Images were acquired using Olympus BX51 Widefield microscope connected to a Nikon DS-5M camera.

Immunofluorescence and Confocal Microscopy

Intestinal samples were fixed overnight in paraformaldehyde, L-Lysine pH 7.4 and NaIO4 (PLP buffer). They were then washed, dehydrated in 20% sucrose for at least 4 hours and included in OCT compound (Sakura). 10 µm cryosections were rehydrated, blocked with 0.1M Tris-HCl pH 7.4, 2% FBS, 0.3% Triton X-100 and stained with the following antibodies: anti-mouse PLVAP (clone MECA32, BD Pharmingen), anti-mouse CD34 (clone RAM34, eBioscience) and anti-mouse zonula occludens [ZO-1 (clone ZO1-1A12, Invitrogen)]. Slices were then incubated with the appropriate fluorophore-conjugated secondary antibody. Before imaging, nuclei were counterstained with 4',6-diamidin-2-fenilindolo (DAPI) and slides were mounted in VECTASHIELD® Mounting Media (Cat.H-1000). Coverslips were permanently sealed around the perimeter with nail polish. Slides were stored at +4° C. in the dark till acquisition by Leica TCS SP2 AOBS with Leica Confocal Software. Images were acquired with an oil immersion objective 63× or with HCX PL APO 40× (NA 1.25) oil immersion objective. Fiji software package was used for image analysis and fluorescence quantification.

Statistical Analysis

Statistical analysis was performed using GraphPad Prism software. Values were compared using either a Student's t-test for single variable or one-way ANOVA Bonferroni's multiple comparison test depending on the distribution of the data. Results were represented as Mean±SEM. $*p<0.05$, $p<0.01$, $*p<0.001$.

Results

Figure 2:
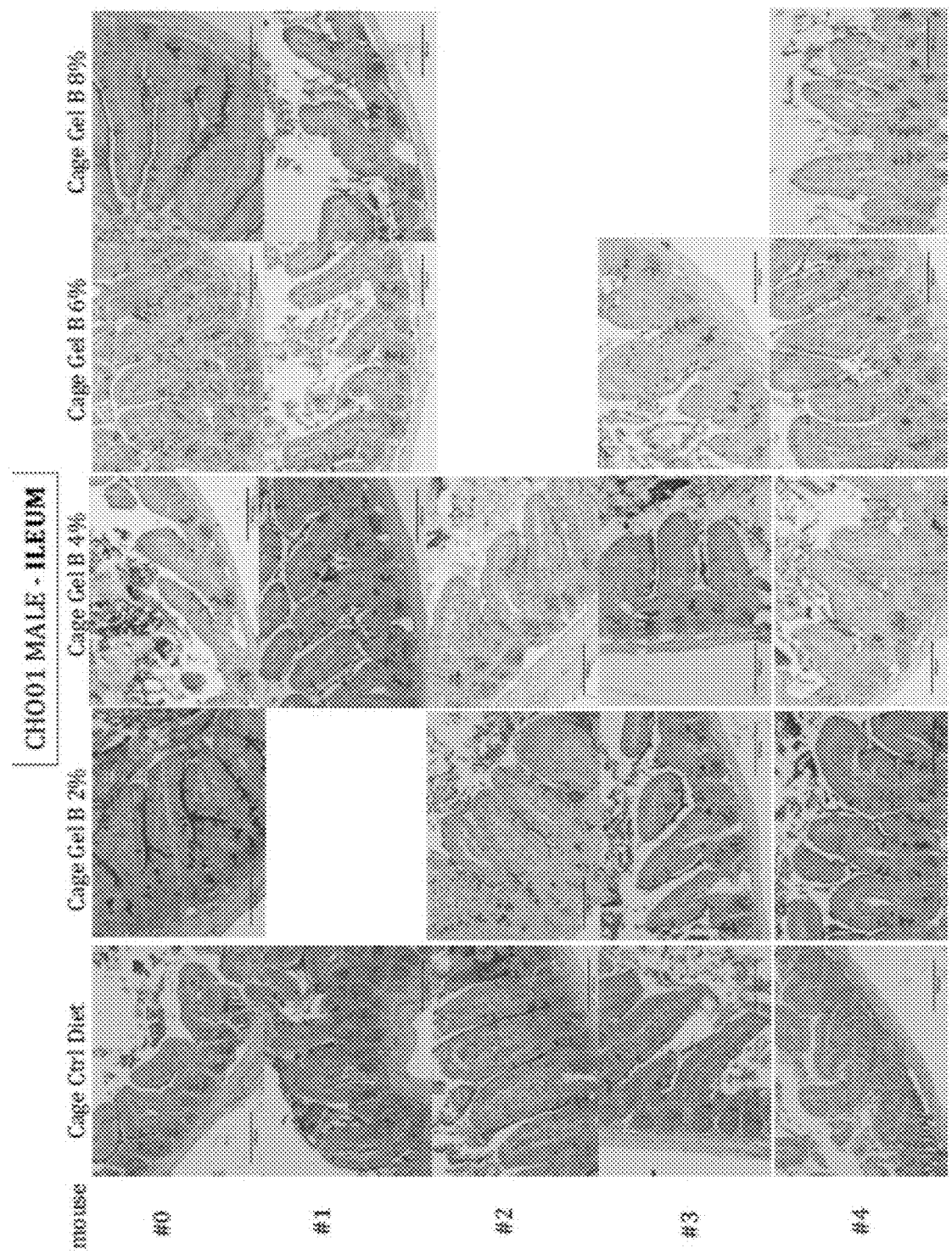
FIG. 2 is an image of the stained ilea of control mice and mice treated with a hydrogel of the invention stained with Alcian Blue-PAS for mucus visualization.
Figure 3:
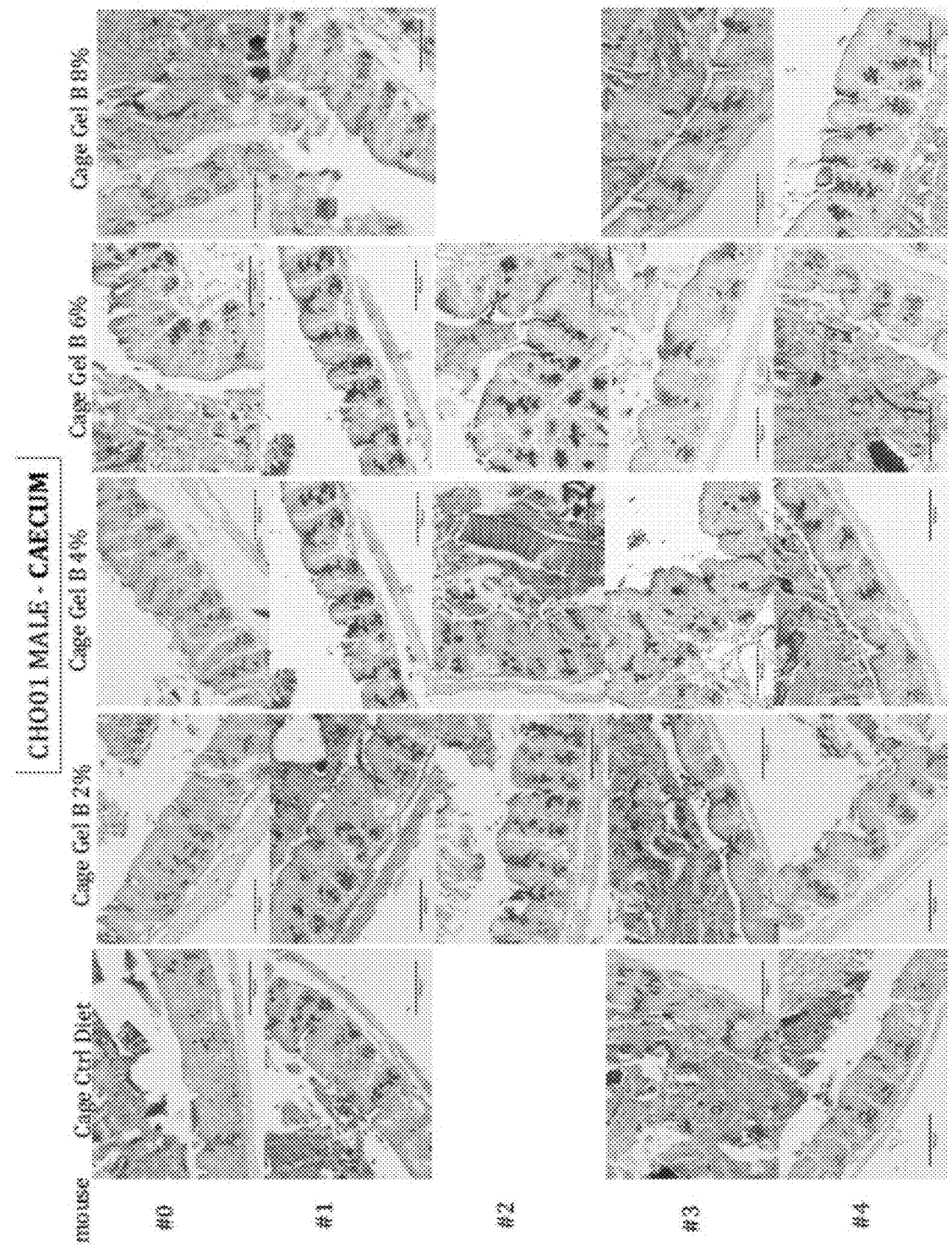
FIG. 3 is an image of the stained caecum of control mice and mice treated with a hydrogel of the invention stained with Alcian Blue-PAS for mucus visualization.

The results of these studies are shown in FIGS. 1-12. FIG. 1 shows wide field microscope images of mouse jejunum sections. Blue staining indicates the presence of mucins. Dark blue dots identify goblet cells responsible of mucus production and are increased in mice receiving the hydrogel relative to control mice. As the mice studied were healthy mice having a normal mucus layer, the results show that the hydrogel promotes mucin production also in normal tissue. A similar result is shown in FIG. 2 for ileal tissue and in FIG. 3 for cecal tissue.

Figure 4:
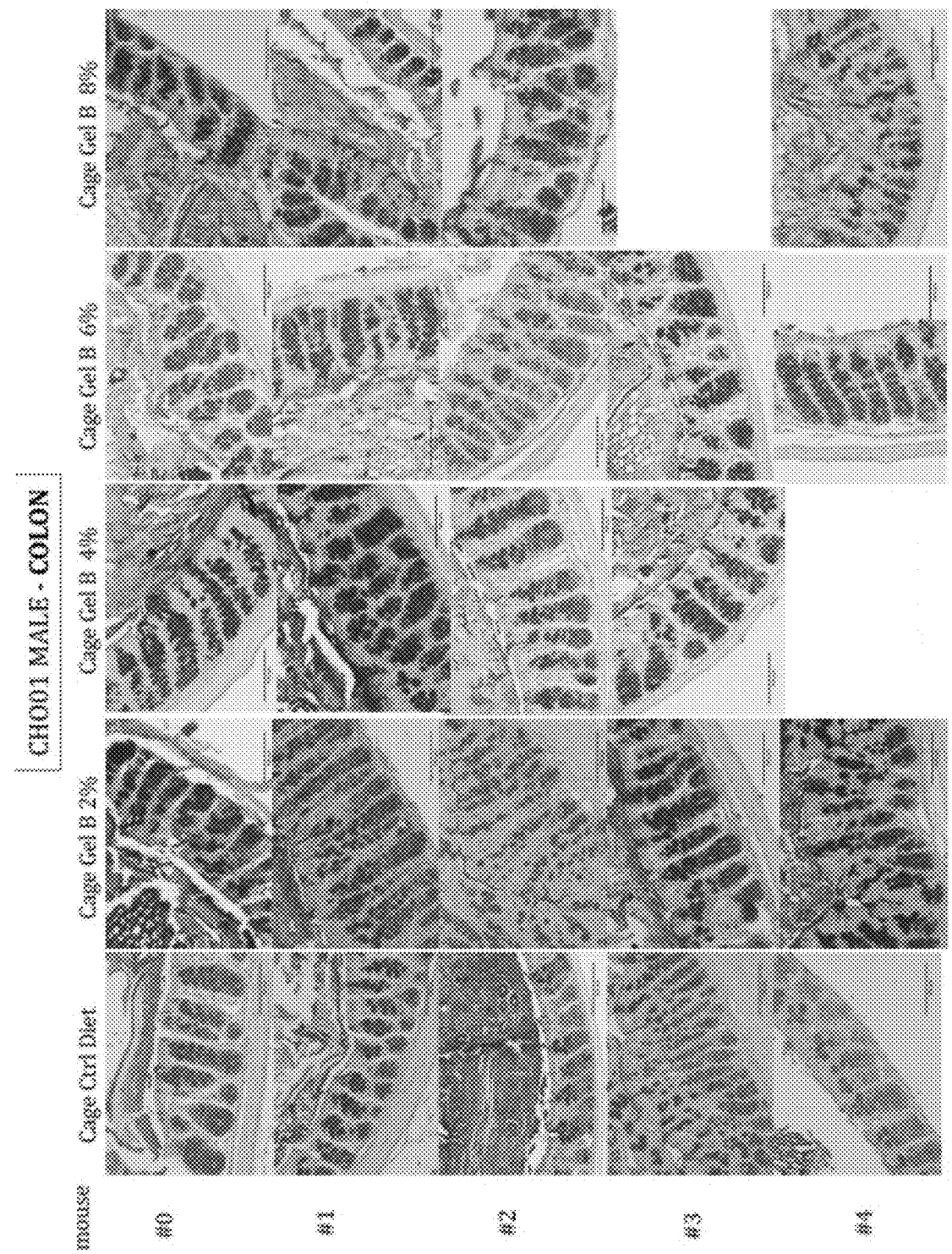
FIG. 4 is an image of the stained colons of control mice and mice treated with a hydrogel of the invention stained with Alcian Blue-PAS for mucus visualization.

FIG. 4 shows results of mucin staining in colonic tissue from control and hydrogel-fed mice. Compared to the other tissues, there is a greater increase in mucin content in colon tissues from the hydrogel groups compared to control group. In particular, the hydrogel groups have a better mucin distribution, i.e. the dark blue staining is more widespread. This portion of the intestinal tract has more bacteria, and is more stressed, than the other tissues, suggesting that the hydrogel has a greater effect in stressed tissues.

Figure 5:
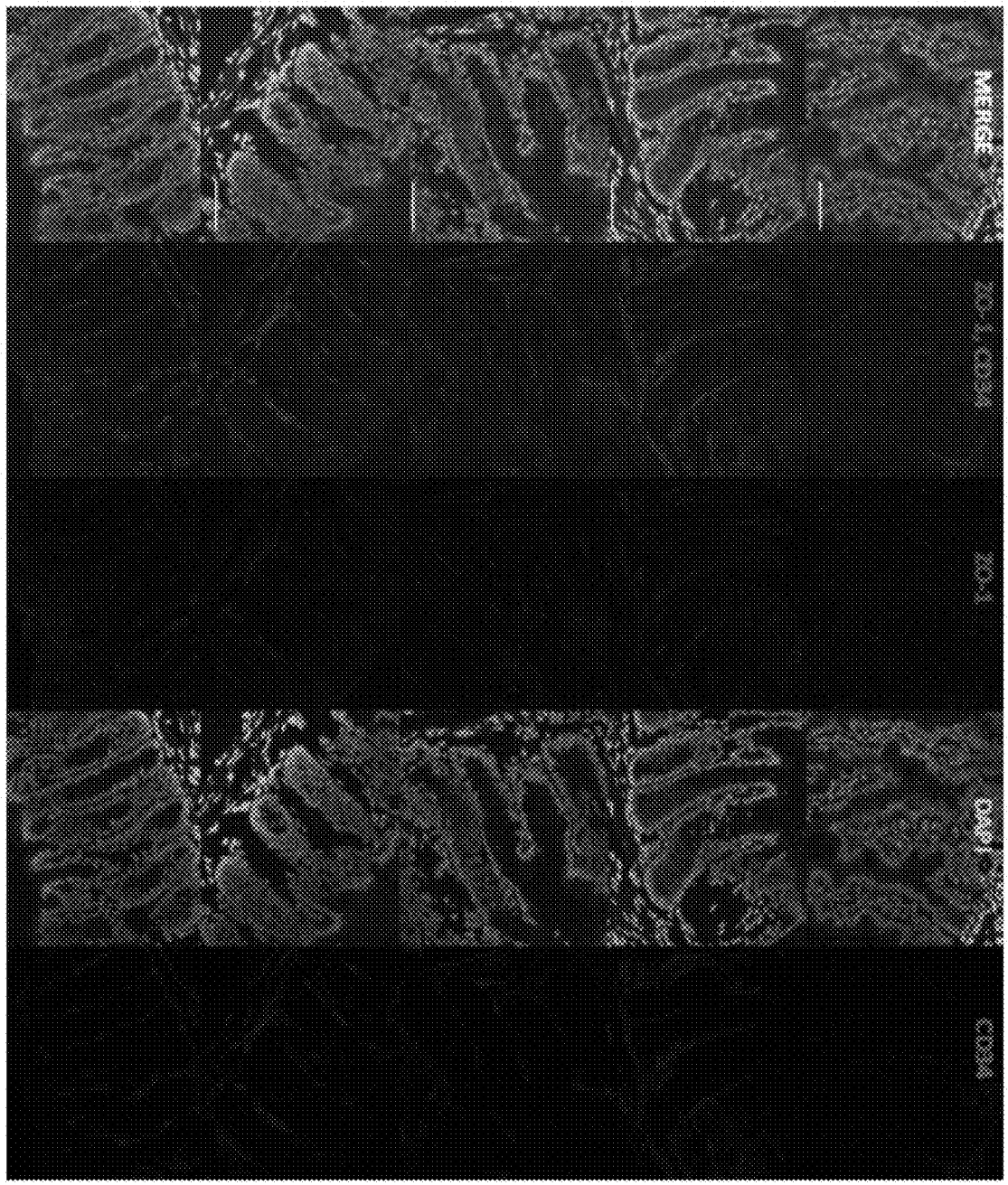
FIG. 5 is an image of the stained colons of the control animals (diet without hydrogel) stained for junctional ZO-1 (ZO-1, component of tight junctions is in red; CD34, marker for intestinal vessels in blue and DAPI marker for nuclei in cyan).

FIG. 5 shows the results of ZO-1 staining (red) in colon tissues from the control group. Images in columns 2 and 3 show a low level of tight junction protein ZO-1.

Figure 6:
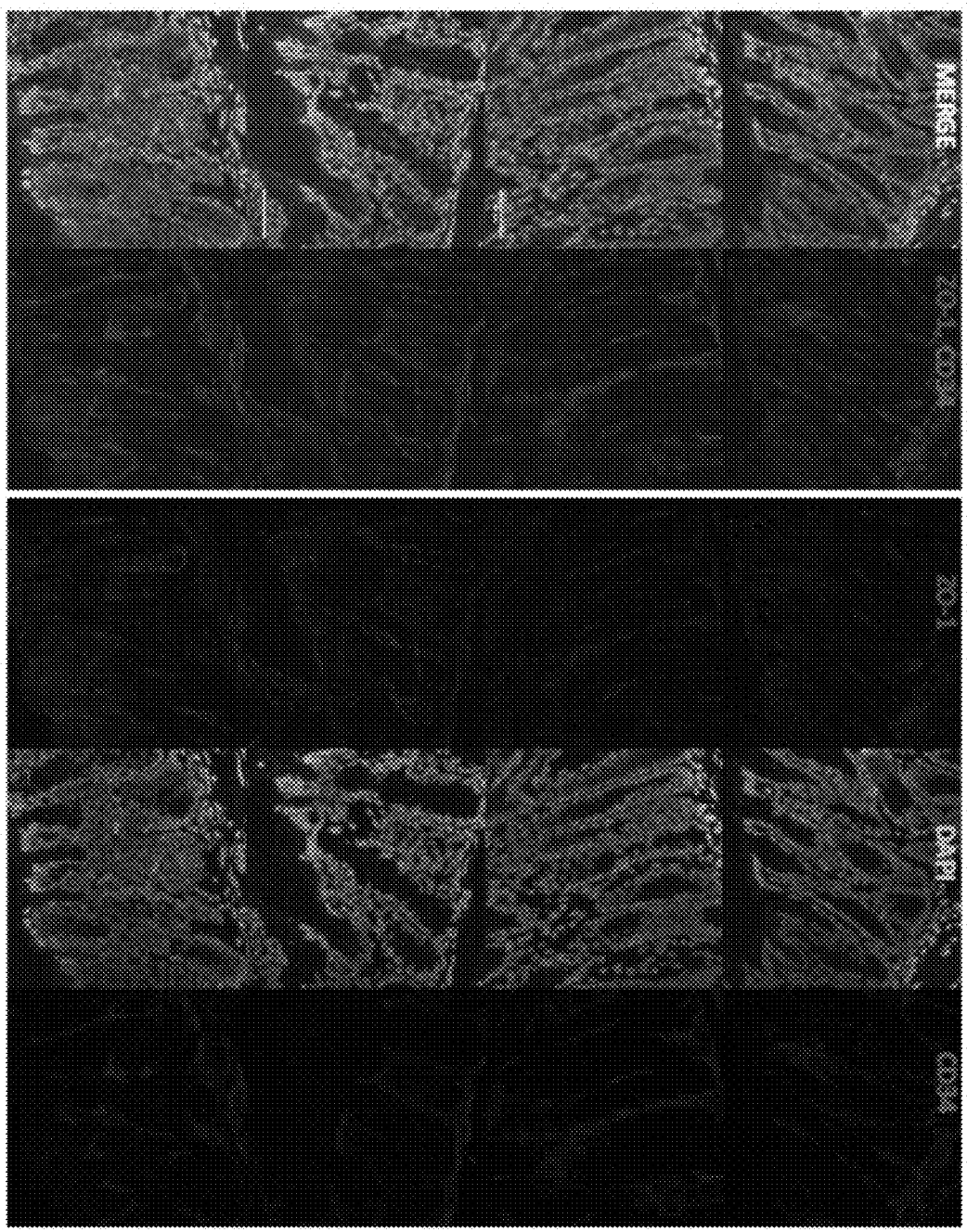
FIG. 6 is an image of the colons of animals treated with 8% of Gel B stained for junctional ZO-1.
Figure 7:
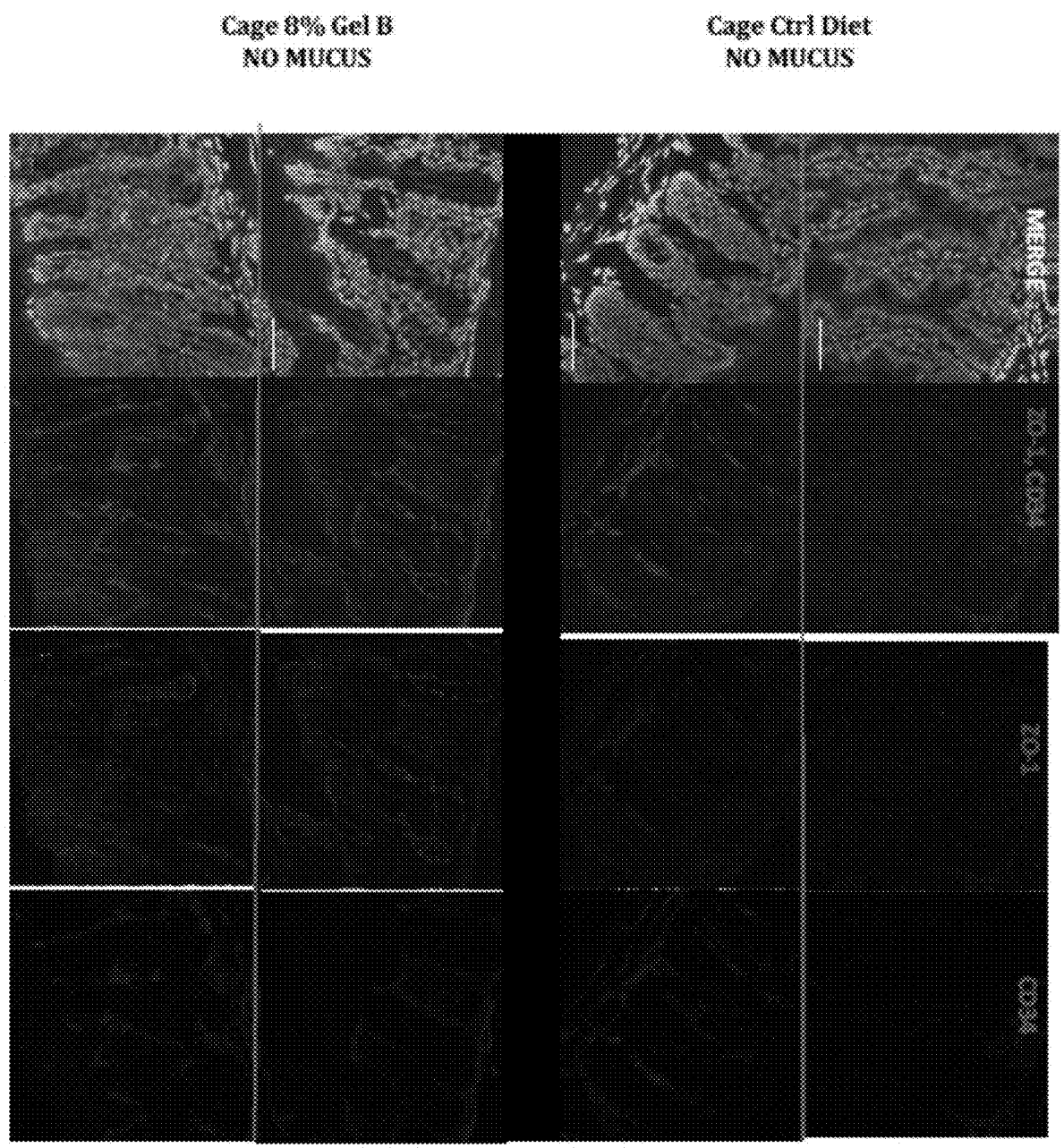
FIG. 7 is an image showing the stained colons of control animals and animals treated with 8% Gel B.
Figure 8:
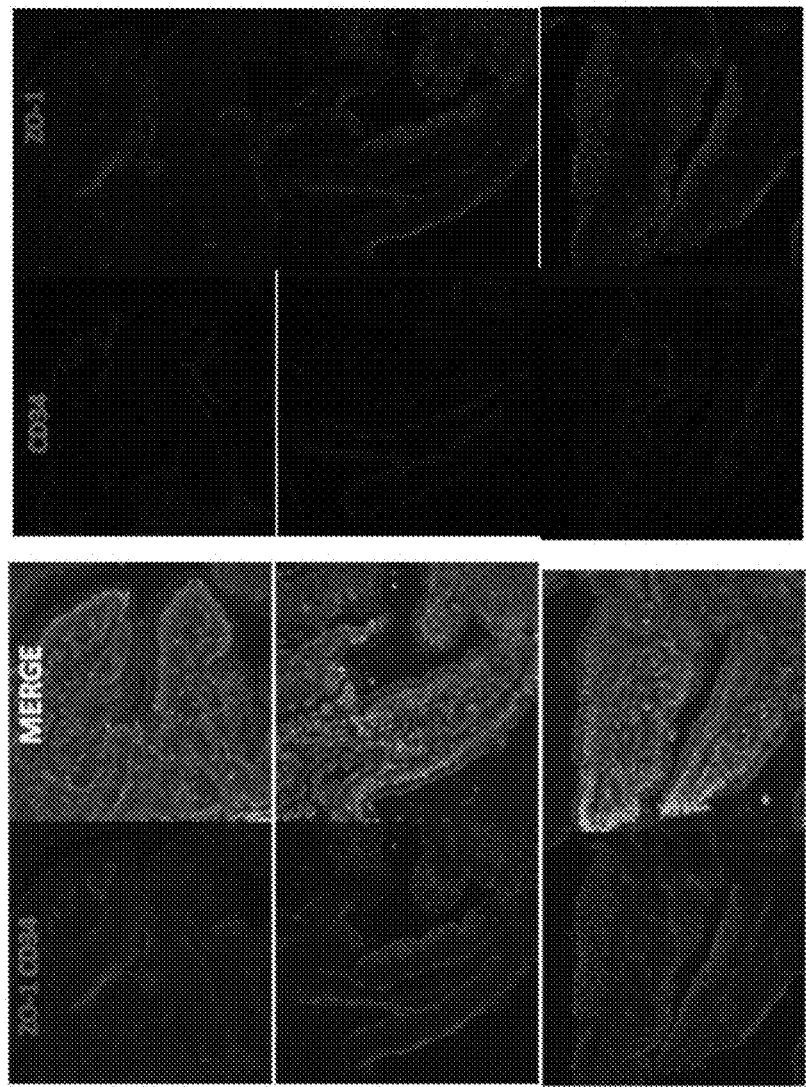
FIG. 8 is an image showing the stained ilea of control animals (ZO-1, component of tight junctions is in red; CD34, marker for intestinal vessels in blue and DAPI marker for nuclei in cyan).
Figure 9:
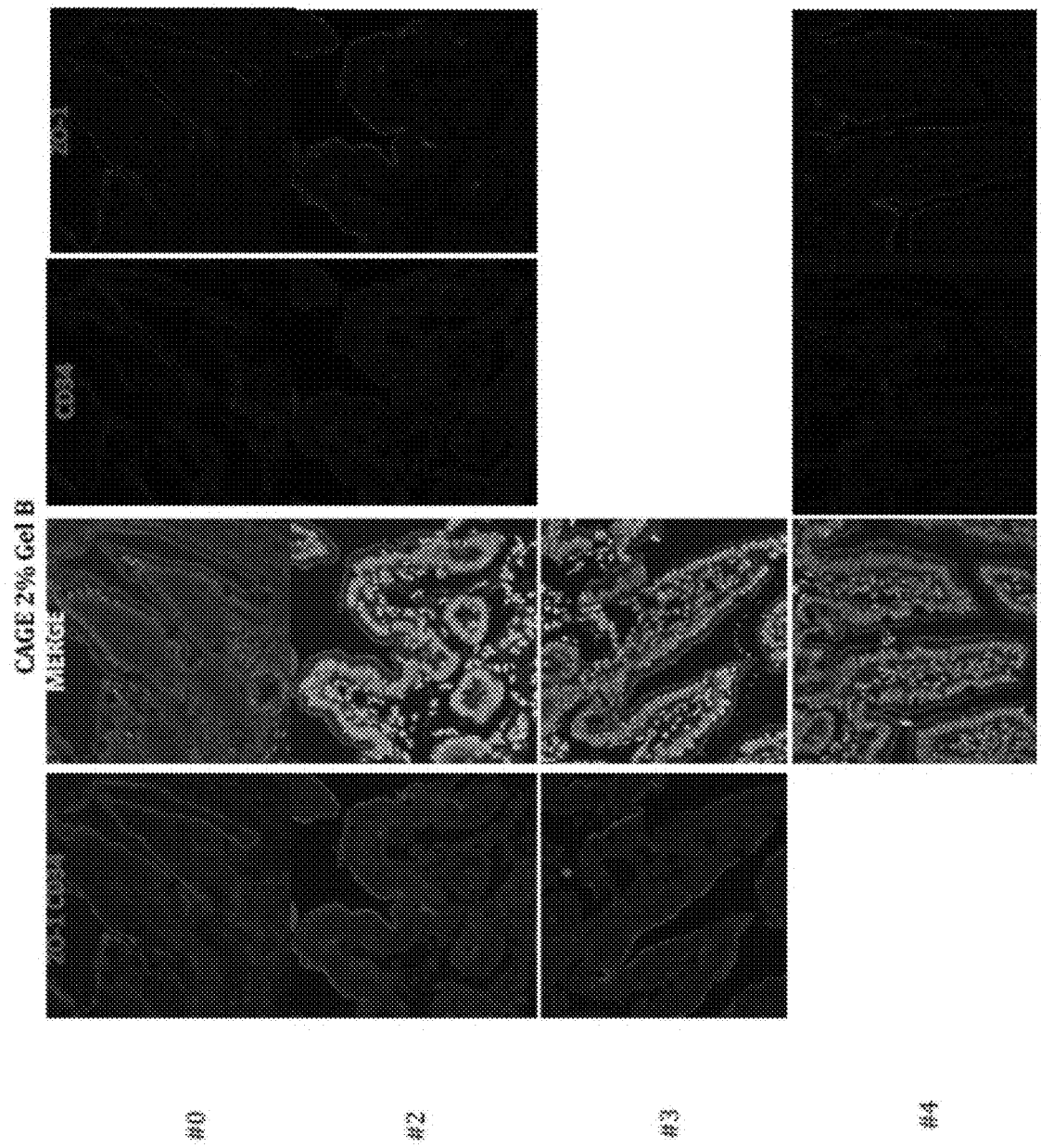
FIG. 9 is an image showing the stained ilea of animals treated with 2% of Gel B.
Figure 10:
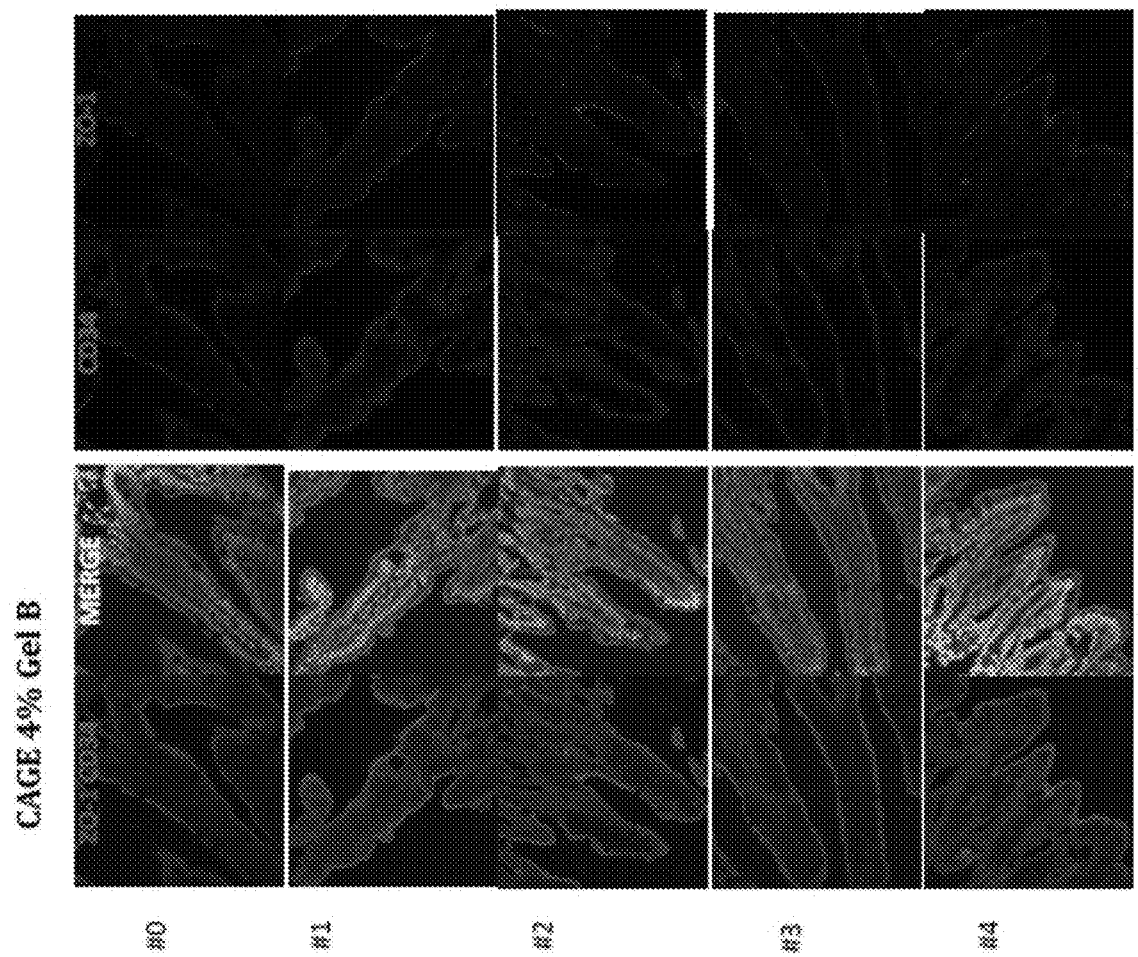
FIG. 10 is an image showing the stained ilea of animals treated with 4% of Gel B.
Figure 11:
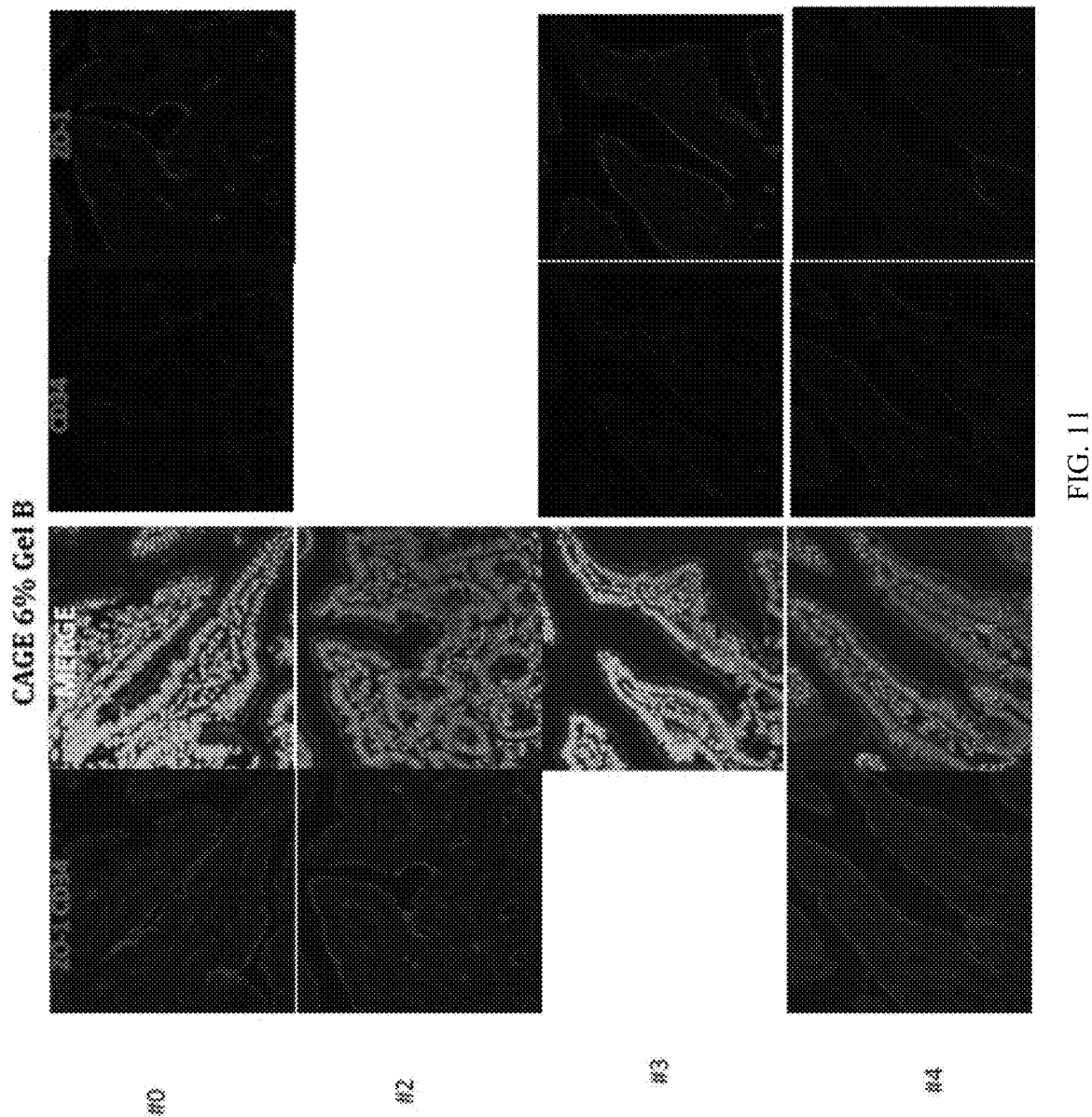
FIG. 11 is an image showing the stained ilea of animals treated with 6% of Gel B.
Figure 12:
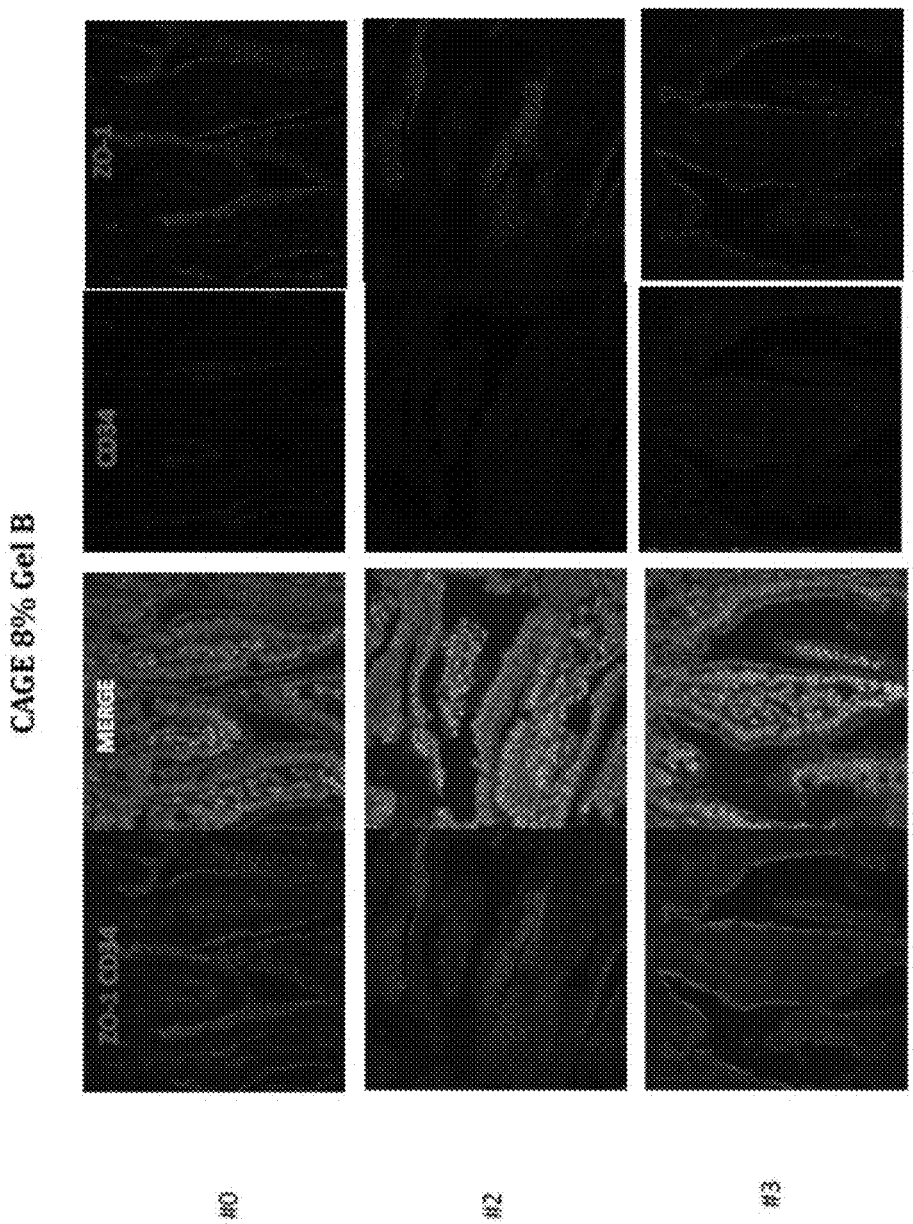
FIG. 12 is an image showing the stained ilea of animals treated with 8% of Gel B.

FIG. 6 shows the results of ZO-1 staining in colon tissue from the 8%-hydrogel supplemented diet group. Compared to the control FIG. 7, this group shows a significant increase in tight junction protein ZO-1 and, thus, an increase in epithelial barrier tightness.

FIGS. 8-12 show the results of ZO-1 staining in ileum tissue. Because there are many bacteria in the ileum, ZO-1 is significantly expressed in normal tissue and there is no observed difference between control and gel-treated products.

The results show that hydrogel-supplemented diets induce intestinal tissue regeneration patterns in mice. In particular, formation of tight junctions was observed in the colon. Moreover, mucus regeneration is observed when a material with proper elastic properties is added to the diet. There is an optimal value of elastic properties of this added material which is responsible for the optimal regeneration. Lower and higher elastic properties are responsible for lower regeneration patterns.

Example 4—In Vitro Studies with Human Tissue Samples

Healthy colon samples were obtained from the healthy tissue of patients undergoing surgery for cancer. The mucosal layer was separated from the muscular layers by a pathologist and transferred to our laboratory in Hank's Balanced Salt Solution (HBSS) at 4° C. supplemented with bacteriostatic antibiotics. The samples blinded.

The clean mucosal layer was washed in HBSS buffer and cut with sterile scalpels into 1 $cm^2$ pieces.

A cave cylinder (borosilicate cloning cylinder, 6×6 mm for mouse samples and 8×8 mm for human samples, BellCo) was glued with surgical glue (Vetbond, 3M, Milan, Italy) on the apical face of the mucosa. The mucosa was then placed on a sterile metal grid, previously washed in fetal bovine serum, in a center well organ culture dish (BD Falcon) and 1 mL of DMEM containing 15% FBS, glutamine, epidermal growth factor (200 ng/ml, Peprotech) and Insulin-Transferrin-Selenium-X (10 µl/ml, Gibco) was used to fill the center of the plate.

Tissues were left for 1 hour at 37° C. in a 5% carbon dioxide incubator to allow mucus reconstitution. At the end of mucus reconstitution, cave cylinders were filled with complete medium, PBS (Phosphate Buffer Saline) and the different Gel formulations, Gel B-01, Gel B-02. Gel B-03 and Gel B-04, respectively. The respective Gel B-01, Gel B-02. Gel B-03 and Gel B-04 formulations were hydrated in PBS under mild agitation and a constant temperature of 37° C. for 30 minutes. Treated tissues were incubated for 2 hours at 37° C. in a 5% carbon dioxide incubator. At the end of incubation tissues were fixed in Carnoy's fixative for 40 minutes and transferred in absolute ethanol and kept at +4° C. for at least 72 hours, before processing and paraffin embedding.

Results

Figure 13:
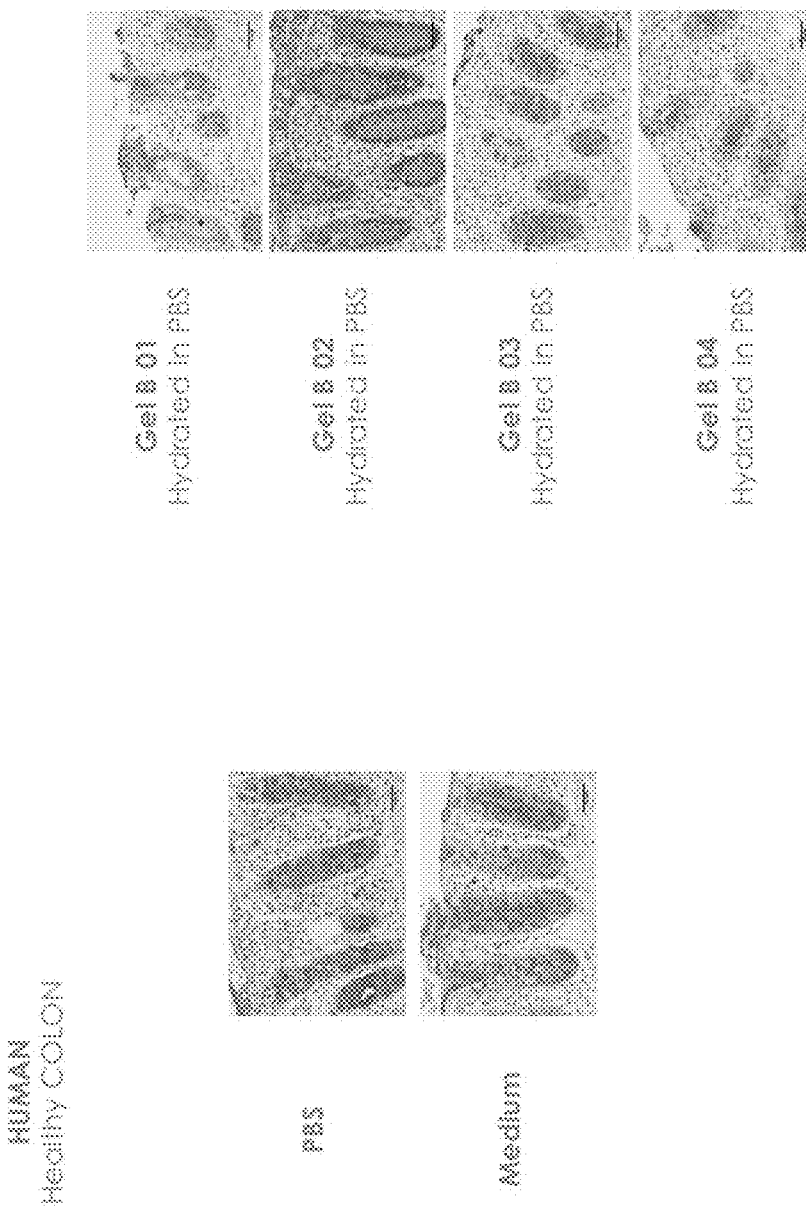
FIG. 13 is an image showing human colon tissue samples that have been treated with medium, PBS, Gel B-01, Gel B-02, Gel B-03 or Gel B-04 stained with Alcian Blue-PAS for mucus visualization.

The results of these studies are shown in FIG. 13, in which the blue staining indicates the mucus layer. The labels Medium and PBS indicate tissue samples which were not treated with hydrogel. Gel B-01, Gel B-02. Gel B-03 and Gel B-04 are as described in Table 1 of Example 1. Hydrogel Gel B-01 was administered as a mixture with citric acid. A clear effect of hydrogel elastic properties on mucus layer regeneration was observed. Gel B-03 shows the best regeneration properties (darker and better uniformly distributed blue areas, with much lower infiltration of inflammatory immune cells). Lower (Gel B-02) and higher (Gel B-04) cross-linking degrees promote a mucus regeneration pattern, but to a lesser degree than Gel B-03 and not optimal distribution of mucins (elongated patterns). Uncrosslinked carboxymethylcellulose (Gel B-01) shows poor regeneration properties, as well as the PBS tissue samples.

Example 5—In Vivo Mucositis Model

Gastrointestinal mucositis is a common side effect of anticancer chemotherapy such as 5-Fluorouracil (5-FU), a commonly used anticancer therapy for colon cancer. Not only does mucositis decrease the quality of life in most cancer patients because of its associated intense pain, it is also a high-risk factor for sepsis with neutropenia and malnutrition. This association, thus, renders mucositis a clinically important disease and any complementary agents capable of reducing mucositis-related symptoms would bring great value. This study was conducted to determine whether a hydrogel administered after a short course of 5-17U could alter the disease process and minimize the severity of mucositis.

Methods

Fifteen, 8 weeks old, male C57B6/J mice obtained from Charles River were utilized for this study. Animals were housed with access to pelleted food and water ad libitum in a temperature-controlled environment with a 12-hour light/dark cycle. AU received a bolus of 5-FU (450 mg/kg intraperitoneally) on day one followed by 3 more days of 5-FU 50 mg/kg intraperitoneally. Following 5-FU exposure, mice were randomly divided into three experimental groups with 5 mice in each group; 1) Chow diet alone, 2) Chow supplemented with Gel B-02 2%, or 3) Chow supplemented with GelB-02 4% for 5 days. Body weights were recorded every day, and the animals were sacrificed on the 5th day after the last 5-FU administration.

Statistical Analysis

For the results of all experimental analyses, means and standard deviation in each group were calculated. Statistical significance of the means in each group was tested using one-way ANOVA or two-way ANOVA with Bonferroni post-test for multiple comparison, at a significance level of $\alpha=0.05$.

Results

Figure 14:
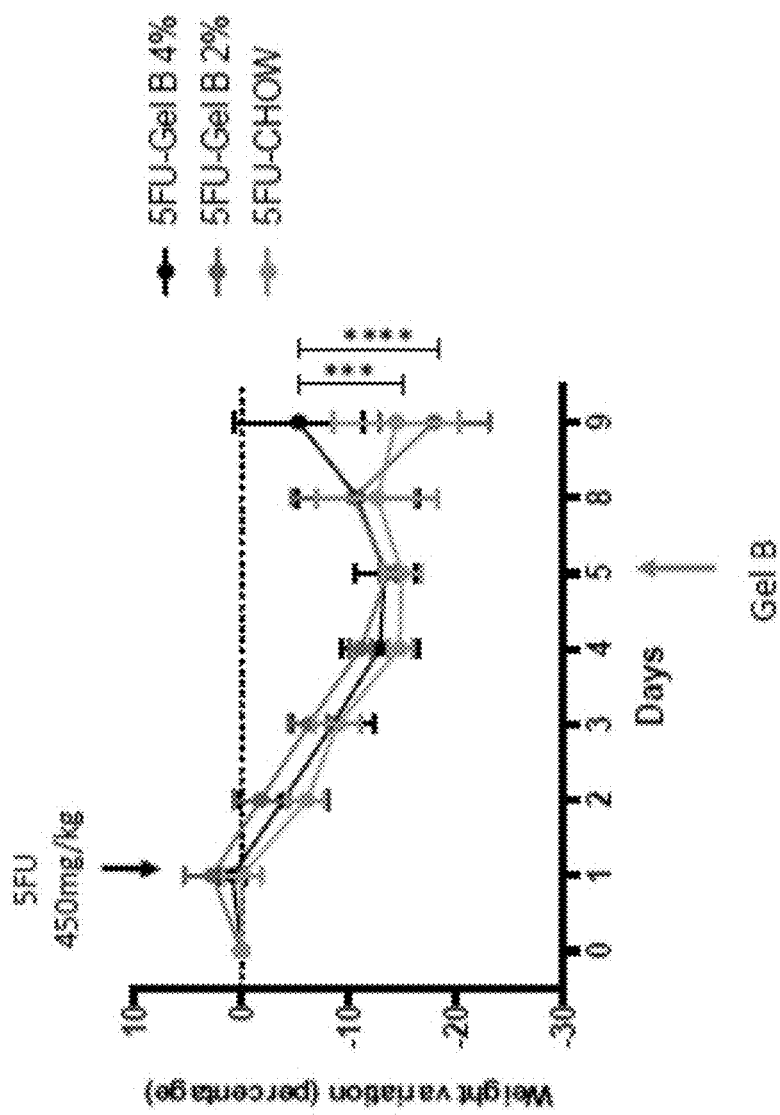
FIG. 14 is a graph showing weight variation in percentage of body weight of mice fed with Chow diet, GelB-02 2% supplemented diet and GelB-02 4% supplemented diet; n=5 per group (***$P<0.01$ calculated by two-way ANOVA).

Daily administration of 5-FU resulted in rapid weight loss in all groups. The weight loss continued in all groups except the group exposed to Gel B-02 4%, which showed a progressive recovery in weight over the 4 days of hydrogel administration with a statistically significant difference at day 9, compared to Chow diet fed mice ($p<0.01$) (FIG. 14).

Figure 15:
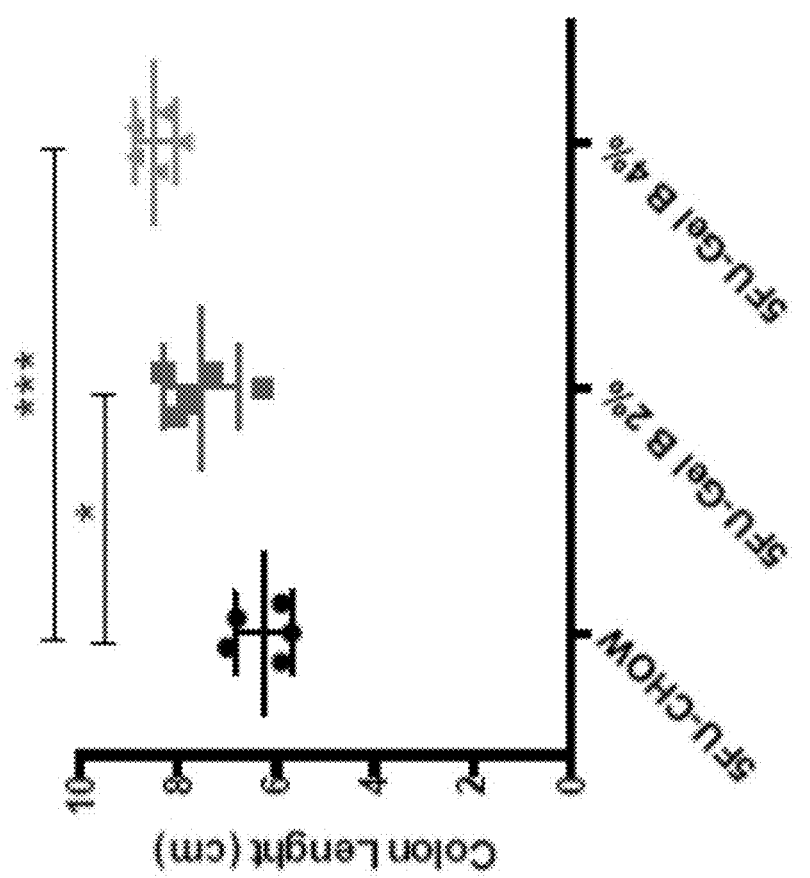
FIG. 15 shows Colon Length in centimeters at day 9 of mice fed with Chow diet, GelB-02 2% supplemented diet and GelB-02 4% supplemented; n=5 per group (*$P<0.05$; ***$P<0.01$ calculated by one-way ANOVA).

At day 9 colon tissues were collected and colon shortening was evaluated measuring colon length as a parameter of intestinal inflammation. The colon of mice fed Chow supplemented with Gel B-02 2% and Chow supplemented with Gel B-02 4% showed a significant ($p<0.05$ and $p<0.01$, respectively) improvement in colon length when compared to Chow control diet alone and almost completely reverted back to normal length (FIG. 15).

Example 6—Ex Vivo Organ Culture and Gel Study

The purpose of the study was to explore the ability of hydrogels with different elasticity properties to preserve intestinal tissue health and regenerative properties.

Samples were obtained from the healthy colon tissue of C57BL6/J mice obtained from Charles River Labs.

The clean mucosal layer was washed in Dulbecco's Modified Eagle Medium (DMEM) containing 15% fetal bovine serum (FBS), glutamine (2 mM), epidermal growth factor (200 ng/ml, Peprotech) and Insulin-Transferrin-Selenium-X (10 μl/ml, Gibco) and cut with sterile scalpels into 1 $cm^2$ pieces.

A cave cylinder (borosilicate cloning cylinder, 6×6 mm for mouse samples, BellCo) was glued with surgical glue (Vetbond, 3M, Milan, Italy) on the apical face of the mucosa. The mucosa was then placed on a sterile metal grid, previously washed in fetal bovine serum, in a center well organ culture dish (BD Falcon) and 1 mL of DMEM containing 15% FBS, glutamine, epidermal growth factor (200 ng/ml, Peprotech) and Insulin-Transferrin-Selenium-X (10 μl/ml, Gibco) was used to fill the center of the plate.

Colon tissues were incubated with hydrogels with different elasticity, namely Gel B01 (hydrogel with the lowest elasticity), 02, 03 and 04 (hydrogels with progressively higher elasticity) for 2 hours at 37° C., upon mucus reconstitution (1 hour at 37° C. without hydrogels). PBS and Medium treated tissues have been used as negative and positive controls, respectively.

Upon incubation, tissues were Carnoy fixed and embedded in paraffin to obtain tissue sections. The tissue was exposed to the media or the hydrogels only from the side which is normally exposed to the intestinal contents. Sections were hence stained with Alcian Blue/PAS (to visualize the mucus and mucus-secreting cells) or with Ki-67 antibody (to detect cell proliferation).

Gels referenced in this example were prepared as described in Example 1, Tables 1 and 2 and were characterized as described in Example 2.

Figure 16:
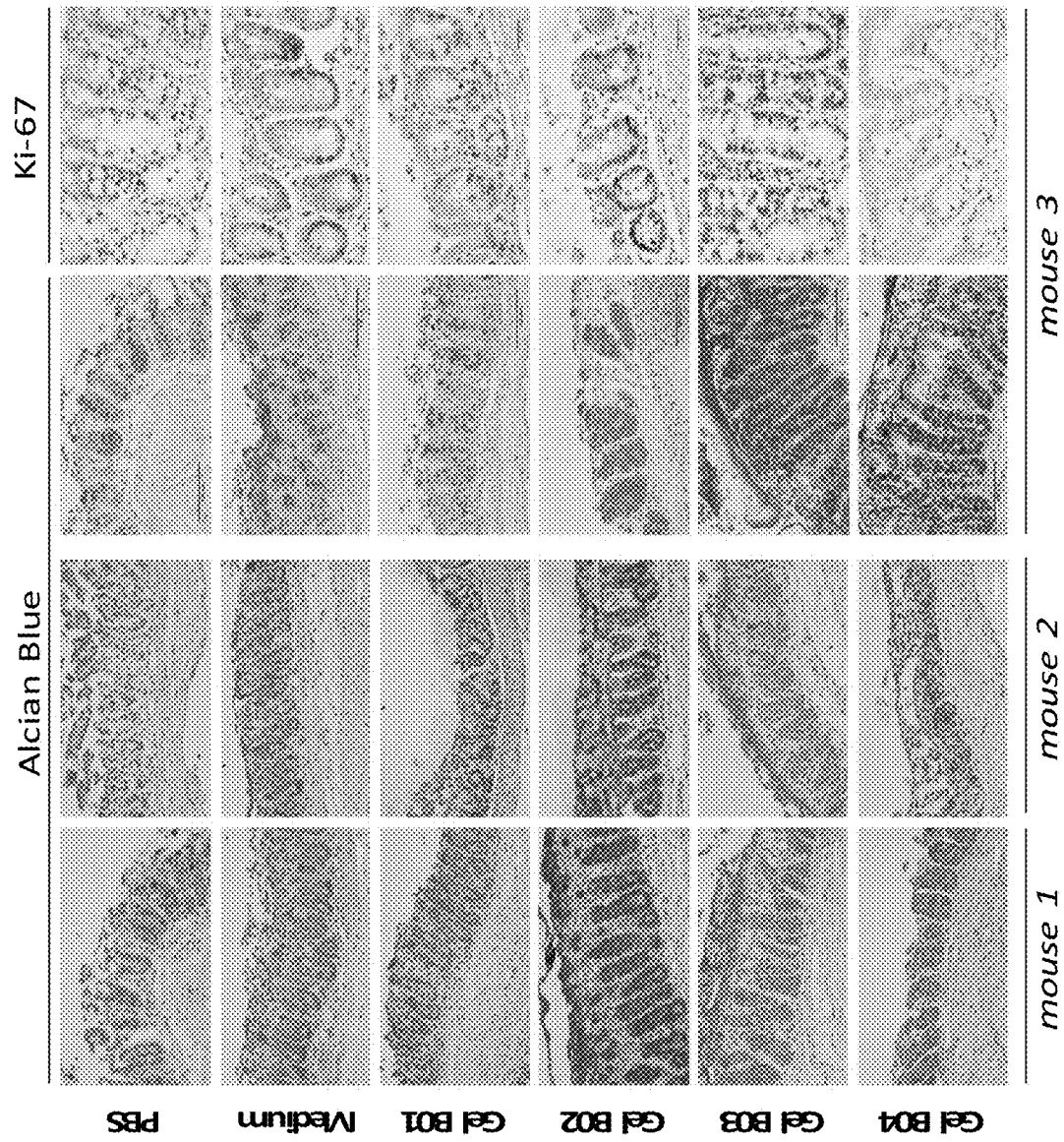
FIG. 16 is an image showing colon sections of mice incubated with various CMC/CA hydrogels with different levels of elasticity stained for mucus visualization (Alcian Blue/PAS and Ki67 IHC).

Results:

A) Comparison Between CMC/CA Hydrogels With Different Levels of Elasticity:

From the analysis of additional independent experiments (with different mice and also with human tissue from Example 4) it emerged that Gel B02 and Gel B03 are those that better preserve tissue architecture integrity, mucus layer production and integrity (as shown by the Alcian Blue/PAS staining in FIG. 16) and proliferative capacity (as shown by the presence of Ki-67 positive nuclei in brown). These data suggest that Gel B02 and B03 are those the tissue is more compliant with, and their elasticity range is preferable.

B) Comparison Between CMC/CA Hydrogels With Different Levels Elasticity to CMC/PEGDE Hydrogels with Comparable Elasticity: Part 1.

Figure 17:
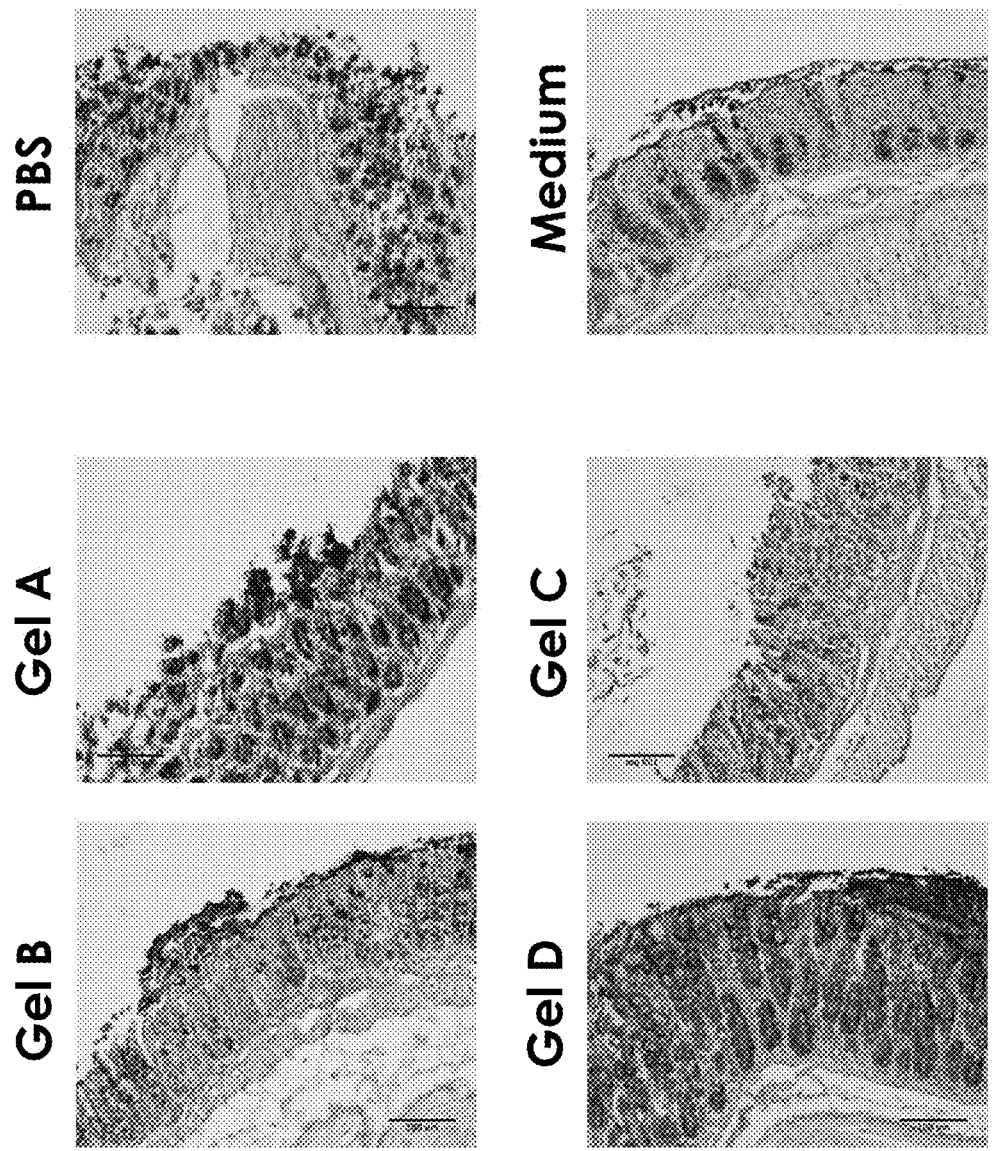
FIG. 17 is an image showing stained colon sections of mice incubated with various CMC/CA hydrogels with different levels of elasticity or CMC/PEGDE hydrogels with comparable elasticity to that of the CMC/CA hydrogels.

From the analysis of Gels with similar or different stiffness properties (i.e Gel B-02 compared to Gel D, Gel A compared to Gel C; Gels B-02 and D compared to Gels A and C) in FIG. 17, it emerged that Gel B-02 and Gel D have the better but similar preservation effect on colon tissues, better preserving architecture integrity and mucus layer production and integrity. Whereas, Gel A and Gel C have a poor effect on tissue integrity while Gel A is better than Gel C. This suggests that Gel B-02 and Gel D are those the tissue is more compliant with, due their higher and similar viscoelastic properties, compared to those of Gel A and Gel C.

It was observed that Tissue health and regeneration is similar between CMC hydrogels when changing the type of CMC or cross-linker but effected by the level of elasticity.

It appears that Hydrogels for promoting epithelium and mucosa health and regeneration could be obtained by using CMC from high or low viscosity, as well as different types of cross-linkers, as long as the elasticity is at the right range.

C) Comparison Between CMC/CA Hydrogels With Different Levels Elasticity to PEGDA Hydrogels with Comparable Elasticity: Part 2.

Figure 18:
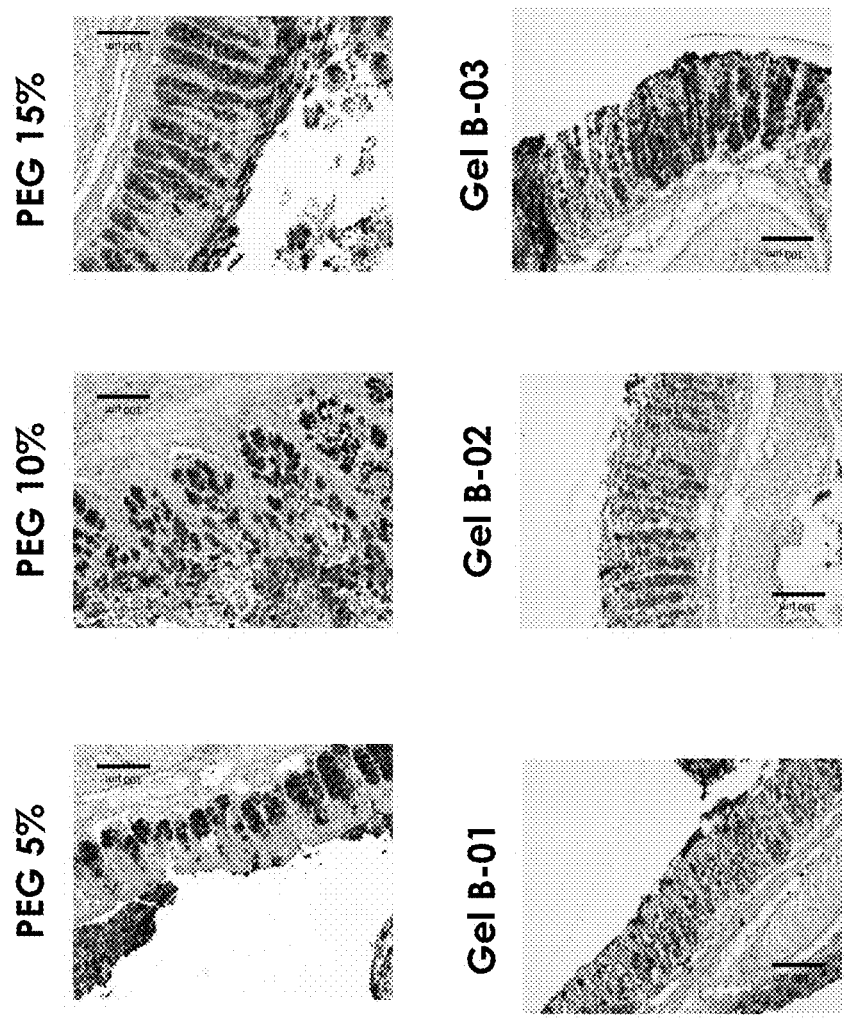
FIG. 18 is an image showing stained colon sections of mice incubated with various CMC/CA hydrogels with different levels of elasticity or PEGDA hydrogels with comparable elasticity to that of the CMC/CA hydrogels.

From the analysis of Gel B and PEGDA gels shown in FIG. 18, it emerged that compounds with comparable viscoelastic/stiffness properties (Gel B-01 and PEGDA 5%; Gel B-02 and PEGDA 10%; Gel B-03 and PEGDA 15%) show a similar effect on colon tissues, in term of architecture preservation and mucus layer production and integrity. In conclusion, modulating viscoelastic properties of the gels give rise to different tissue responses.

It was observed that tissue health and regeneration is affected by the level of elasticity when using hydrogels with PEG backbone as well. The optimal effect on the tissue which was achieved by the PEG hydrogels was between elasticity levels provided by PEG 5% to PEG 15%. However, The CMC based hydrogels provided better results in comparable ranges of elasticity. This observation suggests that there is an additional effect which is related to the composition matter on the regeneration pattern. This could be related to microbiota effects or others.

From these results and observations, it is apparent that a wide range of hydrogels can be used for epithelial tissue and mucosa health and regeneration. The hydrogel elasticity is a crucial parameter. Hydrogel composition seems to provide additional effect on the regeneration patterns, therefore we propose using hydrogels coupling proper ranges of elasticity and proper composition of matter. Preferably hydrogels with higher absorption properties and better biocompatibility should be used since they allow more effective and also safer administration and use.

D) Comparison Between Uncrosslinked Fibers With Different Levels of Elasticity.

Figure 19:
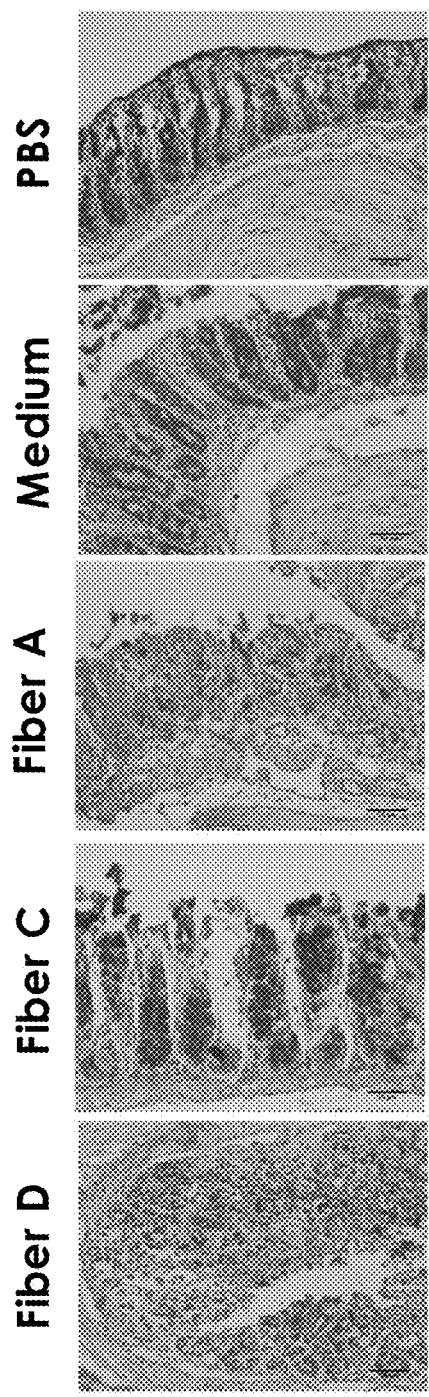
FIG. 19 is an image showing stained colon sections of mice incubated with various uncrosslinked fibers with different levels of elasticity.

From this analysis it emerged that Fiber C appears to preserve some tissue architecture integrity and mucus layer production and integrity (as shown by the Alcian Blue/PAS staining in FIG. 19). Fiber A and Fiber D appear to have a negative effect on tissue and mucus integrity.

The observations from this analysis show that tissue health and regeneration is not improved through the mechanical properties of functional fibers, especially not by insoluble fiber like Microcrystalline Cellulose. Fibers generating higher level of elasticity such as glucomannan show slight improvement which is related to their higher elasticity. However, uncrosslinked fibers are not providing proper regeneration pattern through mechanical effects. Therefore, it can be concluded that Glucomannan and other soluble polysaccharides are not desirable for use in their uncrosslinked form.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed is:

1. A method for treating a disturbed intestinal permeability in a subject in need thereof, comprising administering to the gastrointestinal tract of the subject a therapeutically effective amount of a crosslinked hydrogel having an elastic modulus (G') of about 500 Pa to about 10,000 Pa, wherein the hydrogel is a polysaccharide comprising carboxymethylcellulose.

2. The method of claim 1 wherein the carboxymethylcellulose is high viscosity carboxymethylcellulose.

3. The method of claim 2 wherein the carboxymethylcellulose is covalently crosslinked.

4. The method of claim 3 wherein the carboxymethylcellulose is crosslinked with a polycarboxylic acid.

5. The method of claim 3 wherein the carboxymethylcellulose is crosslinked with citric acid or a bifunctional PEG.

6. The method of claim 1, wherein the elastic modulus (G') is about 600 Pa to about 9,000 Pa.

7. The method of claim 1, wherein the elastic modulus (G') is about 800 Pa to about 8,000 Pa.

8. The method of claim 1 wherein the carboxymethylcellulose is crosslinked with PEGDE or citric acid.

9. The method of claim 1, wherein the hydrogel is high viscosity carboxymethylcellulose crosslinked with citric acid.

10. The method of claim 1, wherein the hydrogel is orally administered to the gastrointestinal tract.

11. The method of claim 1, wherein the elastic modulus (G') is maintained during passage throughout the gastrointestinal tract of the subject.

12. The method of claim 1, wherein the elastic modulus (G') when swollen in simulated intestinal fluid (SIF) is within 20% of the G' when swollen in a 1:8 mixture of simulated gastric fluid (SGF)/water.

13. The method of claim 1, wherein the subject has been diagnosed with non-alcoholic steatohepatitis (NASH) or non-alcoholic fatty liver disease (NAFLD).

14. The method of claim 1 wherein, the subject has been diagnosed with inflammatory bowel disease (IBD).

15. The method of claim 1, wherein the elastic modulus (G') is about 600 Pa to about 6,000 Pa.

* * * * *